(12) United States Patent
Matthews et al.

(10) Patent No.: US 9,717,780 B2
(45) Date of Patent: Aug. 1, 2017

(54) SHEEP NEMATODE VACCINE

(71) Applicant: Moredun Research Institute, Edinburgh (GB)

(72) Inventors: Jacqueline Matthews, Edinburgh (GB); Alasdair Justice Nisbet, Edinburgh (GB); David Knox, Edinburgh (GB)

(73) Assignee: Moredun Research Institute, Edinburgh (GB)

( * ) Notice: Subject to any disclaimer, the term of this patent is extended or adjusted under 35 U.S.C. 154(b) by 0 days.

(21) Appl. No.: 14/376,234

(22) PCT Filed: Feb. 4, 2013

(86) PCT No.: PCT/GB2013/050247
§ 371 (c)(1),
(2) Date: Aug. 1, 2014

(87) PCT Pub. No.: WO2013/117912
PCT Pub. Date: Aug. 15, 2013

(65) Prior Publication Data
US 2015/0040251 A1 Feb. 5, 2015

(30) Foreign Application Priority Data

Feb. 7, 2012 (GB) .................... 1202090.5

(51) Int. Cl.
| | | |
|---|---|---|
| *A61K 39/00* | (2006.01) | |
| *A61K 39/38* | (2006.01) | |
| *A61K 39/002* | (2006.01) | |
| *C07K 14/435* | (2006.01) | |
| *C07K 16/18* | (2006.01) | |

(52) U.S. Cl.
CPC ...... *A61K 39/0003* (2013.01); *C07K 14/4354* (2013.01); *C07K 16/18* (2013.01); *A61K 2039/552* (2013.01)

(58) Field of Classification Search
CPC .................................................... A61K 39/00
USPC ................................ 424/184.1, 185.1, 265.1
See application file for complete search history.

(56) References Cited

FOREIGN PATENT DOCUMENTS

WO WO95/09182 * 4/1995 ........... C07K 14/435

OTHER PUBLICATIONS

Redmond, D.L., et al. International Journal for Parasitology, vol. 36, pp. 277-286, 2006.*
De Maere et al. "Identification of potential protective antigens of *Ostertagia ostertagi* with local antibody probes" *Parasitology* 125:383-391 (2002).
European Patent Office Communication pursuant to Rule 164(2)(b) and Article 94(3) EPC corresponding to European Patent Application No. 13702826.2 (11 pages) (dated Dec. 1, 2015).
International Search Report and the Written Opinion of the International Searching Authority corresponding to International Patent Application No. PCT/GB2013/050247 (20 pages) (dated Jun. 4, 2013).
Smith et al. "Proteomic analysis of excretory/secretory products released by *Teladorsagia circumcincta* larvae early post-infection" *Parasite Immunology* 31:10-19 (2009).

* cited by examiner

*Primary Examiner* — Rodney P Swartz
(74) *Attorney, Agent, or Firm* — Myers Bigel, P.A.

(57) ABSTRACT

The present invention is based upon the identification of a number of antigens derived from species of the genus *Teladorsagia*, which can be used to raise immune responses in animals—particularly those animals susceptible or predisposed to infection by (or with) one or more *Teladorsagia* species. The antigens may be exploited to provide compositions and vaccines for raising protective immune responses in animals—the protective immune responses serving to reduce, prevent, treat or eliminate *Teladorsagia* infections/infestations.

8 Claims, 19 Drawing Sheets

Figure 1A:
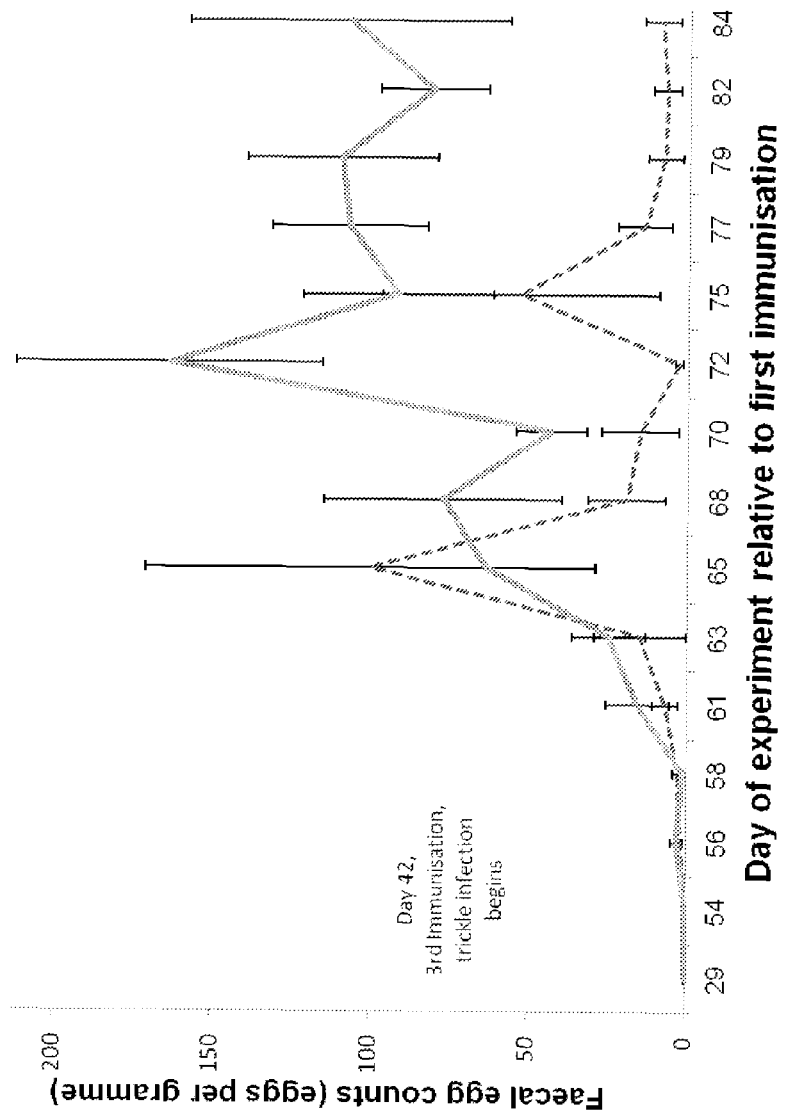

1. Tci-MIF-1
2. Tci-APY-1
3. Tci-MEP-1
4. Tci-CF-1
5. Tci-TGH-2
6. Tci-20ES
7. Tci-SAA-1
8. Tci-ASP-1

SEQUENCE LISTING

<160> NUMBER OF SEQ ID NOS: 8

<210> SEQ ID NO 1
<211> LENGTH: 162
<212> TYPE: PRT
<213> ORGANISM: Teladorsagia circumcincta

<400> SEQUENCE: 1

```
Met Phe Cys Arg Val Thr Val Ala Val Leu Leu Leu Ala Val Ser Ala
1               5                   10                  15

His Ala Gly Phe Phe Asp Asp Val Ser Gly Leu Ala Ser Asp Val Gly
            20                  25                  30

Asp Phe Phe Thr Lys Gln Phe Asn Asn Val Lys Asp Leu Phe Ala Asn
        35                  40                  45

Asn Gln Ser Glu Leu Glu Lys Asn Ile Gln Arg Val Lys Asp Leu Leu
    50                  55                  60

Met Ala Ile Lys Glu Lys Ala Lys Met Leu Glu Pro Met Ala Asn Asp
65                  70                  75                  80

Ala Gln Lys Lys Thr Ile Ser Glu Val Asn Asn Tyr Met Gln Gln Val
                85                  90                  95
```

```
Asp Ala Phe Gly Ala Gln Val Lys Arg Asp Gly Glu Ala Lys Phe Glu
            100                 105                 110

Gln Asn Lys Ala Lys Trp Gln Asp Met Leu Asn Asn Ile Phe Glu Lys
        115                 120                 125

Gly Gly Leu Glu Asn Val Met Lys Leu Met Asn Leu Lys Ser Ala Thr
    130                 135                 140

Gln Cys Thr Val Met Ala Ala Leu Ile Ala Pro Val Ile Leu Ala Phe
145                 150                 155                 160

Thr Arg

<210> SEQ ID NO 2
<211> LENGTH: 115
<212> TYPE: PRT
<213> ORGANISM: Teladorsagia circumcincta

<400> SEQUENCE: 2

Met Pro Val Phe Ser Phe His Thr Asn Val Ser Ala Asp Lys Val Thr
1               5                   10                  15

Pro Asp Leu Leu Lys Gln Ile Ser Ser Val Val Ala Arg Ile Leu His
            20                  25                  30

Lys Pro Glu Ser Tyr Val Cys Val His Val Val Pro Asp Gln Gln Met
        35                  40                  45

Ile Phe Asp Gly Thr Asp Gly Pro Cys Gly Val Gly Val Leu Lys Ser
    50                  55                  60

Ile Gly Gly Val Gly Gly Ser Lys Asn Asn Glu His Ala Lys Ala Leu
65                  70                  75                  80

Phe Ala Leu Ile Lys Asp His Leu Gly Ile Ala Gly Asn Arg Met Tyr
                85                  90                  95

Ile Glu Phe Ile Asp Ile Gly Ala Ala Asp Ile Ala Phe Asn Ser Arg
            100                 105                 110

Thr Phe Ala
        115

<210> SEQ ID NO 3
<211> LENGTH: 236
<212> TYPE: PRT
<213> ORGANISM: Teladorsagia circumcincta

<400> SEQUENCE: 3

Met Phe Thr Pro Ile Gly Ile Ala Val Leu Tyr Leu Ala Leu Val Thr
1               5                   10                  15

Pro His Ala Lys Ala Gly Phe Cys Cys Pro Ala Asp Leu Asp Gln Thr
            20                  25                  30

Asp Glu Ala Arg Lys Ile Leu Leu Asn Phe His Asn Glu Val Arg Arg
        35                  40                  45

Asp Val Ser Ser Ala Ser Pro Leu Leu Asn Leu Thr Gly Ala Val Leu
    50                  55                  60

Met Arg Asn Val Leu Gly Pro Ala Lys Asn Met Tyr Lys Met Asp Trp
65                  70                  75                  80

Asp Cys Asn Leu Glu Lys Lys Ala Leu Glu Met Ile Ser Pro Cys Thr
                85                  90                  95

Val Pro Leu Pro Ile Asp Thr Ser Ile Pro Gln Asn Leu Ala Gln Trp
            100                 105                 110

Leu Leu Tyr Arg Lys Met Glu Glu Thr Glu Val Leu Glu Lys Ala Pro
        115                 120                 125
```

```
Trp Ser Trp Val Ile Ala Ser Leu Arg Asn Leu Lys Asn Asp Thr Glu
        130                 135                 140

Ala Asp Leu Tyr Asn Trp Lys Ile Arg Thr Ile Ser Asn Ile Leu Asn
145                 150                 155                 160

Trp Arg Asn Thr Lys Val Gly Cys Ala His Lys Val Cys Gln Phe Pro
                165                 170                 175

Thr Gly Thr Asn Met Val Ile Ser Cys Ala Tyr Gly Gly Asp Lys Leu
                180                 185                 190

Glu Asn Asn Glu Val Val Trp Gln Lys Gly Pro Thr Cys Glu Cys Asn
                195                 200                 205

Ala Tyr Pro Asp Ser Tyr Cys Cys Asn Asn Leu Cys Asp Thr Lys Ala
210                 215                 220

Ala Ala Ala Leu Arg Glu Glu Pro Cys Lys Ser Asn
225                 230                 235

<210> SEQ ID NO 4
<211> LENGTH: 305
<212> TYPE: PRT
<213> ORGANISM: Teladorsagia circumcincta

<400> SEQUENCE: 4

Met Arg Leu Leu Asn Ser Met Gly Met Gln Glu Pro Pro Asn Val Asp
1               5                   10                  15

Ser Ile Asp Leu Ser Pro Ser Thr Ile Glu Glu Met Leu Glu Ser Leu
                20                  25                  30

Gly Glu Asn Asp Lys Leu Glu Gln Asp Gln Glu Glu Lys Thr Phe Ile
                35                  40                  45

Met Ala Val Asp Pro Ser Asp Gly Ile Asp Pro Asp Met Leu Val Ala
50                  55                  60

Arg Phe Pro Val Ser Ile Thr Thr Met Val Arg Lys Val Ser Arg Ala
65                  70                  75                  80

Tyr Leu His Val Tyr Leu His Val Ser Glu Pro Leu Pro Glu Pro Glu
                85                  90                  95

Ile Val Thr Val Val Arg Glu Arg Leu Leu Asn Gly Asp Val Gly
                100                 105                 110

Asp Ile Val Ala Thr Asn Pro Val Glu Ile Gln Arg Ser Gly Lys Ala
                115                 120                 125

Val Leu Pro Leu Arg Ala Ser Asp Val Glu Arg Trp Trp Lys Ser Glu
                130                 135                 140

Pro Ile Leu Gly Leu Tyr Val Val Ala Met Leu Asn Gly Glu Asn Ile
145                 150                 155                 160

Ala Val His Pro Gln Gln Asp His His Ala Arg His Thr Met Phe Met
                165                 170                 175

Ser Val Ile Leu Ala Ser Asp Ala Lys Ser Arg Gly Lys Arg Ser Pro
                180                 185                 190

Ser Val Cys Met Pro Glu Asp Gln Glu Pro Gly Cys Cys Leu Tyr Asp
                195                 200                 205

Leu Ile Val Asp Phe Gln Gln Ile Gly Trp Lys Phe Ile Ile Ala Pro
210                 215                 220

His Lys Tyr Asn Ala Tyr Met Cys Arg Gly Asp Cys Ser Val Asn His
225                 230                 235                 240

Thr His Val Thr Arg Ser Gly His Thr Lys Val Ala Lys Thr Gly Ile
                245                 250                 255

Ile Thr Arg Gln Asp Ala Thr Gly Asn Gln Gly Met Cys Cys His Pro
                260                 265                 270
```

```
Ala Glu Tyr Asp Ala Val Arg Met Ile Tyr Met Asn Gly Asp Asn Gln
            275                 280                 285

Val Thr Met Ala Arg Val Pro Gly Met Ile Ala Arg Lys Cys Thr Cys
    290                 295                 300

Ser
305

<210> SEQ ID NO 5
<211> LENGTH: 364
<212> TYPE: PRT
<213> ORGANISM: Teladorsagia circumcincta

<400> SEQUENCE: 5

Met Ser Leu Leu Phe Leu Leu Ile Pro His Leu Phe Ala Ala Thr
1               5                   10                  15

Val Lys Gln Gln Tyr Ser Gly Gly Val Lys Pro Leu Thr Glu Leu Arg
                20                  25                  30

Thr Asp Leu Ile Asp Lys Thr Lys Gly Ser Ile Glu Phe Ala Arg
            35                  40                  45

Leu Gly Gln His Ile Ser Pro Lys Asp Phe Gly Ala Trp Asn His Phe
    50                  55                  60

Thr Ser Phe Ile Glu Arg His Asp Lys Val Tyr Arg Asn Glu Ser Glu
65                  70                  75                  80

Ala Leu Lys Arg Phe Gly Ile Phe Lys Arg Asn Leu Glu Ile Ile Arg
                85                  90                  95

Ser Ala Gln Glu Asn Asp Lys Gly Thr Ala Ile Tyr Gly Ile Asn Gln
                100                 105                 110

Phe Ala Asp Leu Ser Pro Glu Glu Phe Lys Lys Thr His Leu Pro His
            115                 120                 125

Thr Trp Lys Gln Pro Asp His Pro Asn Arg Ile Val Asp Leu Ala Ala
    130                 135                 140

Glu Gly Val Asp Pro Lys Glu Pro Leu Pro Glu Ser Phe Asp Trp Arg
145                 150                 155                 160

Glu His Gly Ala Val Thr Lys Val Lys Thr Glu Gly His Cys Ala Ala
                165                 170                 175

Cys Trp Ala Phe Ser Val Thr Gly Asn Ile Glu Gly Gln Trp Phe Leu
            180                 185                 190

Ala Lys Lys Lys Leu Val Ser Leu Ser Ala Gln Gln Leu Leu Asp Cys
        195                 200                 205

Asp Val Val Asp Glu Gly Cys Asn Gly Gly Phe Pro Leu Asp Ala Tyr
    210                 215                 220

Lys Glu Ile Val Arg Met Gly Gly Leu Glu Pro Glu Asp Lys Tyr Pro
225                 230                 235                 240

Tyr Glu Ala Lys Ala Glu Gln Cys Arg Leu Val Pro Ser Asp Ile Ala
                245                 250                 255

Val Tyr Ile Asn Gly Ser Val Glu Leu Pro His Asp Glu Glu Lys Met
            260                 265                 270

Arg Ala Trp Leu Val Lys Gly Pro Ile Ser Ile Gly Ile Thr Val
        275                 280                 285

Asp Asp Ile Gln Phe Tyr Lys Gly Gly Val Ser Arg Pro Thr Thr Cys
    290                 295                 300

Arg Leu Ser Ser Met Ile His Gly Ala Leu Leu Val Gly Tyr Gly Val
305                 310                 315                 320

Glu Lys Asn Ile Pro Tyr Trp Ile Ile Lys Asn Ser Trp Gly Pro Asn
```

```
                    325                 330                 335
Trp Gly Glu Asp Gly Tyr Tyr Arg Met Val Arg Gly Glu Asn Ala Cys
                340                 345                 350
Arg Ile Asn Arg Phe Pro Thr Ser Ala Val Val Leu
            355                 360

<210> SEQ ID NO 6
<211> LENGTH: 339
<212> TYPE: PRT
<213> ORGANISM: Teladorsagia circumcincta

<400> SEQUENCE: 6

Met Leu Leu Tyr Ile Leu Ser Leu Val Leu Ile Asp Ala Leu Pro
1               5                   10                  15
Pro Gly Tyr Pro Asp Gly Lys Glu His Gly Ser Arg Pro Thr Ile Arg
                20                  25                  30
Ser Leu Pro Asp Gly Ser Thr Glu Tyr Lys Leu Leu Ile Val Thr Asp
            35                  40                  45
Met Asp Lys Asp Ser Lys Ala Gly Glu Trp Thr Trp Arg Ala Val Thr
    50                  55                  60
Arg Glu Gly Arg Leu Thr Leu Ser Pro Asp Met Ala His Val Ser Ile
65                  70                  75                  80
Ala Trp Asp Glu Asn Ser Glu Arg Asn Leu Thr Ser Ser Met Asn Ile
                85                  90                  95
Lys Gly Arg Ala Met Glu Leu Ser Asp Leu Ser Val Phe His Asn Arg
                100                 105                 110
Ile Leu Thr Pro Asp Asp Arg Thr Gly Leu Ile Ser Glu Ile Lys Asn
            115                 120                 125
Asn Lys Met Ile Pro Trp Val Phe Leu Asn Ser Gly Pro Gly Asn Thr
    130                 135                 140
Thr Ser Pro Phe Lys Cys Glu Trp Met Thr Ile Lys Asp Asp Val Leu
145                 150                 155                 160
Tyr Val Gly Gly His Gly Asn Glu Phe Arg Asn Lys Gln Gly Glu Ile
                165                 170                 175
Val His Arg Asn Asn Leu Trp Ile Lys Thr Val Thr Pro Glu Gly Glu
                180                 185                 190
Val Thr Asn Val Asp Trp Thr Asp Val Phe Asn Asn Leu Arg Asn Ala
            195                 200                 205
Val Gly Ile Ser Glu Pro Gly Tyr Leu Thr His Glu Ala Val Gln Trp
    210                 215                 220
Ser Glu Lys Gln Gly His Trp Tyr Phe Leu Pro Arg Lys Glu Ser Lys
225                 230                 235                 240
Thr Val Tyr Val Glu Glu Asp Glu Lys Lys Gly Thr Asp Leu Leu
                245                 250                 255
Ile Ile Gly Asn Pro Asp Leu Asp Gln Phe Glu Thr Lys Arg Ile Gly
                260                 265                 270
Val Leu Arg Pro Glu Arg Gly Tyr Ser Ala Phe Asp Phe Ile Pro Gly
            275                 280                 285
Thr Asp Asp Lys Ile Ile Val Ala Leu Lys Ser Lys Glu Val Thr Asp
    290                 295                 300
Glu Pro Thr Glu Thr Tyr Val Thr Val Phe Thr Ile Asp Gly Glu Ile
305                 310                 315                 320
Leu Leu Asp Asp Gln Lys Leu Asp Gly Asn Tyr Lys Phe Glu Gly Leu
                325                 330                 335
```

Tyr Phe Ile

<210> SEQ ID NO 7
<211> LENGTH: 498
<212> TYPE: PRT
<213> ORGANISM: Teladorsagia circumcincta

<400> SEQUENCE: 7

Met Arg Leu Ala Val Leu Leu Val Leu Val Ser Ala Gln Ala
1               5                   10                  15

Gly Leu Leu Asp Lys Val Lys Asp Phe Phe Lys Gly Gly Asn Phe Gly
                20                  25                  30

Glu Lys Thr Lys Thr Ala Thr Leu Ser Lys Phe Lys Lys Leu Phe Glu
            35                  40                  45

Lys Thr Gly Ile Leu Ser Leu Gly Asn Lys Leu Ala Glu Met Arg Ser
50                  55                  60

Lys Val Met Lys Lys Leu Glu Leu Ser Lys Ala Lys Lys Ala Glu Val
65                  70                  75                  80

Asp Arg Lys Leu Lys Glu Val Glu Glu Arg Met Asp Asn Thr Val Glu
                85                  90                  95

Asn Leu Lys Asp Thr Ile Phe Glu Ile Asn Ala Val Lys Asn Val Gly
            100                 105                 110

Glu Ser Leu Phe Gln Ser Asp Ile Leu Leu Thr Lys Arg Gln Val Glu
        115                 120                 125

Glu Val Met Asp Gly Val Glu Gly Gly Arg Pro Lys Arg Gln Ala Phe
130                 135                 140

Lys Asp Gln Asn Tyr Pro Asn Thr Thr Trp Gln Gln Gly Val Phe Tyr
145                 150                 155                 160

Arg Phe Asp Asp Ser Ala Asp Tyr Tyr Thr Arg Lys Val Phe Glu Met
                165                 170                 175

Gly Thr Lys Gln Trp Glu Glu Ala Thr Cys Ile Asp Phe Lys Glu Asp
            180                 185                 190

Lys Glu Lys Lys Ala Glu Asn Ser Ile Ile Leu Ile Lys Glu Asp Gly
        195                 200                 205

Cys Trp Ser Tyr Val Gly Gln Val Gly Gly Glu Gln Pro Leu Ser Leu
210                 215                 220

Gly Asp Gly Cys Glu Gln Val Gly Ile Ala Thr His Glu Leu Gly His
225                 230                 235                 240

Ala Leu Gly Leu Phe His Thr Met Ser Arg Tyr Asp Arg Asp Asp Phe
                245                 250                 255

Ile Thr Val Val Leu Glu Asn Val Val Glu Gly Phe Val Asp Gln Tyr
            260                 265                 270

Ile Lys Glu Thr Pro Gln Thr Thr Asn Tyr Gly Phe Thr Tyr Asp
        275                 280                 285

Tyr Gly Ser Ile Met His Tyr Gly Ala Ser Ser Ala Ser His Asn Asn
290                 295                 300

Lys Pro Thr Met Val Ala Asn Asp Thr Arg Tyr Gln Glu Ser Met Gly
305                 310                 315                 320

Ser Gln Ile Ile Ser Phe Ile Asp Lys Ser Met Ile Asn Asp His Tyr
                325                 330                 335

Asn Cys Lys Ala Asp Cys Pro Lys Ala Thr Ser Ala Lys Cys Gln Asn
            340                 345                 350

Gly Gly Phe Pro His Pro Arg Lys Cys Ser Glu Cys Ile Cys Pro Ser
        355                 360                 365

```
Gly Tyr Gly Gly Ala Leu Cys Asp Gln Arg Pro Thr Gly Cys Gly Gln
    370                 375                 380

Thr Leu Lys Ala Lys Glu Ser Lys Gln Phe Leu Ile Asp Lys Leu Gly
385                 390                 395                 400

Phe Pro Ser Gly Val Arg Asp Glu Phe Thr Phe Cys Asn His Trp Ile
                405                 410                 415

Glu Ala Pro Glu Gly Lys Lys Ile Glu Leu Lys Ile Asn Ser Ile Ser
                420                 425                 430

His Gly Tyr Ala His Asp Gly Cys Ile Leu Gly Gly Val Glu Ile Lys
                435                 440                 445

Thr Ser Glu Asp Gln Thr Arg Thr Gly Phe Arg Phe Cys Ser Pro Asn
450                 455                 460

Asp Arg Asn Thr Val Leu Val Ser Ala Ser Asn Arg Val Pro Ile Ile
465                 470                 475                 480

Thr Phe Asn Arg Ser Gly Gln Gln Gln Ile Ile Leu Glu Tyr Lys Val
                485                 490                 495

Val Ser

<210> SEQ ID NO 8
<211> LENGTH: 160
<212> TYPE: PRT
<213> ORGANISM: Teladorsagia circumcincta

<400> SEQUENCE: 8

Met Leu Arg Ser Ile Leu Leu Ile Leu Val Ser Ala Ser Val Tyr Val
1               5                   10                  15

Ser Val Gln Gly Gln Gly Asn Gly Asp Met Lys Lys Val Glu Leu Tyr
                20                  25                  30

Met Gly Tyr Ala Lys Lys Asp Met Glu Lys Val Arg Glu Phe Leu Lys
                35                  40                  45

Leu Lys Asp Glu Arg Leu Thr Lys Leu Leu Ser Asp Leu Phe Arg Tyr
                50                  55                  60

Leu Asp Lys Thr Thr Phe Glu Trp Met Lys Asp Glu Ala Thr Leu Glu
65                  70                  75                  80

Gln Phe Ile Gln Thr Arg Gly Lys Phe Ser Ser Ala Leu Val His Pro
                85                  90                  95

Asp Val Gln Lys Arg Tyr Lys Asp Asn Arg Lys Leu Trp Ala Phe Arg
                100                 105                 110

Tyr Ala Arg Leu Met Asn Cys Ile Gly Gly Ser Asp Met Gly Arg Ala
                115                 120                 125

Thr Ala Tyr Leu Pro Gly Val Ser Val Gln Glu Lys Glu Glu Thr Leu
                130                 135                 140

Arg Tyr Ser Leu Lys Leu Glu Arg Thr Cys Ala Tyr Thr Tyr Phe Arg
145                 150                 155                 160
```

SHEEP NEMATODE VACCINE

RELATED APPLICATIONS

This application is a 35 U.S.C. §371 national stage application of PCT Application No. PCT/GB2013/050247, filed on Feb. 4, 2013, which claims priority from British Application No. 1202090.5, filed on Feb. 7, 2012, the contents of which are incorporated herein by reference in their entireties. The above-referenced PCT International Application was published as International Publication No. WO 2013/117912 A1 on Aug. 15, 2013.

STATEMENT REGARDING ELECTRONIC FILING OF A SEQUENCE LISTING

A Sequence Listing in ASCII text format, submitted under 37 C.F.R. §1.821, entitled 9013-135TS_ST25.txt, 19,533 bytes in size, generated on Jul. 31, 2014 and filed via EFS-Web, is provided in lieu of a paper copy. This Sequence Listing is hereby incorporated by reference into the specification for its disclosures.

FIELD OF THE INVENTION

The present invention relates to nematode antigens capable of raising host immune responses. In particular, the invention provides vaccines for use in protecting against and/or reducing instances of *Teladorsagia* infections.

BACKGROUND OF THE INVENTION

*Teladorsagia circumcincta* (previously known as *Ostertagia circumcincta*) is the major cause of parasitic gastroenteritis in small ruminants in temperate regions. This nematode is controlled primarily by anthelmintics; however resistance is widespread and field isolates have often been found to be insensitive to a number of different anthelmintic classes (Bartley et al., 2004; Wrigley et al., 2006). *T. circumcincta* resides within the abomasum (or true stomach) of small ruminants and primarily causes disease in animals during their first year of grazing. It is a major cause of production losses, estimated to cost the UK sheep industry alone in excess of £80 M per annum (Nieuwhof & Bishop, 2005). The associated clinical signs range from suppressed appetite to diarrhoea, dehydration and death; however, the major impact of teladorsagiosis is its effect on lamb productivity via a reduction in weight gain (Gibson and Everett, 1976).

Protective immunity against challenge with *T. circumcincta* develops after continual ('trickle') infection over a number of weeks (Seaton et al., 1989). The degree of immunity that develops depends on a number of factors including, level of parasite challenge, age of animal and its genotype (Singleton et al., 2011). In ewes that have acquired immunity to *T. circumcincta*, resistance to the parasites can lapse around the time of parturition and early lactation (Houdijk et al., 2005). In terms of anti-parasite effects, the protective immune response has been shown to decrease the establishment of larvae in the abomasal mucosa, slow larval development in the gastric gland and to reduce the egg output of female worms in the abomasal lumen (Balic et al., 2003; Seaton et al., 1989; Smith et al., 1985, 1986; Stear et al., 2004). Experiments that demonstrated successful adoptive transfer between immune and naive sheep using gastric lymph indicate the importance of local immune responses in protective mechanisms against *T. circumcincta* (Smith et al., 1986). The precise mechanisms remain to be defined, but roles for both immediate hypersensitivity reactions and local antigen specific IgA have been highlighted (Smith et al., 1986; 1987). Furthermore, antigen-specific IgA responses have been correlated with reductions in nematode length (Halliday et al., 2007; Smith et al. 2009), whereas IgE responses have been correlated with a reduction in faecal egg counts in grazing lambs (Huntley et al., 2001).

As sheep can acquire a protective immune response against *T. circumcincta* in natural and experimental circumstances, vaccination represents a possible alternative for control.

SUMMARY OF THE INVENTION

The present invention is based upon the identification of a number of antigens derived from species of the genus *Teladorsagia*, which can be used to raise immune responses in animals—particularly those animals susceptible or predisposed to infection by (or with) one or more *Teladorsagia* species. The antigens provided by this invention may be exploited to provide compositions and vaccines for raising protective immune responses in animals—the protective immune responses serving to reduce, prevent, treat or eliminate *Teladorsagia* infections/infestations.

In a first aspect, the present invention provides one or more *Teladorsagia* antigen(s) or a fragment thereof, for use in raising an immune response in an animal.

As stated, the inventors have discovered that the immune responses elicited by the *Teladorsagia* antigens of this invention protect animals against infection/infestation with nematode parasites belonging to the *Teladorsagia* genus. An immune response which protects against infection/infestation by/with a pathogen may be a referred to as a "protective response". In the context of this invention, the term "protective immune response" may embrace any immune response which facilitates or effects a reduction in host pathogen burden—i.e. the number of pathogenic organisms infecting a host. In other embodiments, and in the case of animals infected with *Teladorsagia* parasites, a protective immune response elicited through use of the antigen(s) described herein may result in a reduction in the host faecal egg count (FEC: namely, the number of parasite eggs per gramme (EPG) of faeces—occurring as a result of suppression of egg output from female parasites in the abomasal lumen) and/or a decrease in the numbers of parasitic larvae establishing in the abomasal mucosa or a reduction in the numbers of adult worms (male and/or female) residing in the abomasal lumen. A protective immune response may also slow larval development.

One of skill would appreciate that any reduction in pathogen burden/FEC achieved through use of the antigen(s) described herein, may be compared to the pathogen burden/FEC of an infected animal not exposed to (or administered) the antigen(s) provided by this invention—such animals being devoid of (or lacking) a protective immune response.

A second aspect of this invention provides a composition or vaccine composition comprising one or more of the *Teladorsagia* antigens described herein, for use in raising an immune response in an animal. In one embodiment, the immune response is a protective response.

Additionally, or alternatively, the immune response raised in the animal may prevent the occurrence of further (subsequent/secondary) *Teladorsagia* infections and may also have an effect on the development or survival of co-infecting nematodes of other genera.

In a third aspect, the invention provides the use of one or more *Teladorsagia* antigens or a fragment(s) thereof for the manufacture of a medicament for use in the treatment and/or prevention of an infection/colonisation by/with a *Teladorsagia* pathogen.

In a fourth aspect, the invention provides a method of raising an anti-*Teladorsagia* immune response in an animal, said method comprising the step of administering to an animal, an amount of one or more *Teladorsagia* antigen(s) or fragment(s), sufficient to induce an anti-*Teladorsagia* immune response.

Advantageously, the one or more *Teladorsagia* antigens (or fragments thereof) are derived from *Teladorsagia circumcincta* an ovine parasite infecting the abomasum and causing weight loss, diarrhea and decreased wool production and, in some cases, death.

The term "animal" encompasses animals collectively known as ovine animals. As such, the invention provides antigens and compositions for use in raising immune responses in ovine subjects such as sheep and goats—hosts of the *Teladorsagia circumcincta* parasite.

As such, one embodiment of this invention provides:
(i) one or more antigens derived from *T. circumcincta*;
(ii) compositions and medicaments comprising one or more antigens derived from *T. circumcincta*; and
(iii) methods exploiting one or more antigens derived from *T. circumcincta*;
for use in raising immune responses in ovine animals (including sheep and/or goats).

It should be understood that all references to "antigen" encompass immunogenic components or compounds derived from *Teladorsagia*, and in particular, *T. circumcincta*. In one embodiment, the term "antigen" encompasses *Teladorsagia* antigens which elicit or mimic immune responses occurring during a natural infection. The term natural infection may encompass environmentally/community acquired infections.

The term "antigen" may relate to, for example, *Teladorsagia* proteins and/or peptides (including polypeptides and short peptide chains of one or more amino acids), glycoproteins and/or glycopeptides. In addition, the term "antigen" may relate to carbohydrate molecules. In one embodiment, antigens to be exploited in this invention may be antigens which are present on the surface of *Teladorsagia* cells and/or exposed to the host (ovine) immune system during an infection. One of skill will appreciate that the term "antigens" may also encompass *Teladorsagia* proteins, polypeptides, peptides and/or carbohydrates which are otherwise known as "immunogens".

In one embodiment, the antigens provided by this invention are antigens, which elicit host antibody (for example, IgA and/or IgG) responses. In one embodiment, the antigens are derived from post-infective larval stages of *Teladorsagia* species. The *Teladorsagia* antigens provided by this invention may include those secreted or excreted by *Teladorsagia* larvae in the gastric gland milieu during rapid growth phases within the mucosa or by adult worms in the abomasal lumen. In one embodiment, the antigens are derived from third and/or fourth stage *Teladorsagia* larvae, but may also be secreted by adult stage parasites. Additionally or alternatively, the *Teladorsagia* antigens described herein may comprise pathogen derived immunomodulatory compounds.

In a further embodiment, the term "antigen" encompasses the exemplary *T. circumcincta* (Tci) antigens listed as (i)-(ix) below:
(i) calcium-dependent apyrase-1 (Tci-APY-1).
(ii) astacin-like metalloproteinase-1 (Tci-MEP-1).
(iii) excretory/secretory protein (unknown function: Tci-ES20).
(iv) cathepsin F-1 (Tci-CF-1).
(v) transforming growth protein 2-like protein (a TGFβ homologue: Tci-TGH-2).
(vi) activation associated secretory protein (Tci-ASP-1).
(vii) macrophage migration inhibitory factor (Tci-MIF-1).
(viii) surface associated antigen (Tci-SAA-1).
(ix) a fragment, mutant, variant or derivative of any of (i)-(viii).

An exemplary Tci-SAA-1 sequence is deposited under the accession number CAQ43040 and comprises the sequence given below as SEQ ID NO: 1.

```
                                            SEQ ID NO: 1
mfcrvtvavl llavsahagf fddvsglasd vgdffkqfn nvkdlfannq selekniqrv kdllmaikek akmlepmand aqkktisevn nymqqvdafg aqvkrdgeak feqnkakwqd mlnnifekgg lenvmklmnl ksatqctvma aliapvilaf tr
```

An exemplary Tci-MIF-1 sequence is deposited under the accession number CBI68362 and comprises the sequence given below as SEQ ID NO: 2.

```
                                            SEQ ID NO: 2
Mpvfsfhtnv sadkvtpdll kqissvvari lhkpesyvcv hvvpdqqmif dgtdgpcgvg vlksiggvgg sknnehakal falikdhlgi agnrmyiefi digaadiafn srtfa
```

An exemplary Tci-ASP-1 sequence is deposited under the accession number CBJ15404 and comprises the sequence given below as SEQ ID NO: 3.

```
                                            SEQ ID NO: 3
mftpigiavl ylalvtphak agfccpadld qtdearkill nfhnevrrdv ssaspllnlt gavlmrnvlg paknmykmdw dcnlekkale mispctvplp idtsipqnla qwllyrkmee tevlekapws wviaslrnlk ndteadlynw kirtisniln wrntkvgcah kvcqfptgtn mviscayggd klennevvwq kgptcecnay pdsyccnnlc dtkaaaalre epcksn
```

An exemplary Tci-TGH-2 sequence is deposited under the accession number ACR27078 and comprises the sequence given below as SEQ ID NO: 4.

```
                                            SEQ ID NO: 4
mrllnsmgmq eppnvdsidl spstieemle slgendkleq dqeektfima vdpsdgidpd mlvarfpvsi ttmvrkvsra ylhvylhvse plpepeivtv vvrerllngd vgdivatnpv eiqrsgkavl plrasdverw wksepilgly vvamlngeni avhpqqdhha rhtmfmsvil asdaksrgkr spsvcmpedq epgcclydli vdfqqigwkf iiaphkynay mcrgdcsvnh
```

-continued

```
thvtrsghtk vaktgiitrq datgnqgmcc hpaeydavrm iymngdnqvt marvpgmiar kctcs
```

An exemplary Tci-CF-1 sequence is deposited under the accession number ABA01328 and comprises the sequence given below as SEQ ID NO: 5.

```
                                       SEQ ID NO: 5
msllflllip hlfaatvkqq ysggvkplte lrtdlidkkt kgsiefarlg qhispkdfga wnhftsfier hdkvyrnese alkrfgifkr nleiirsaqe ndkgtaiygi nqfadlspee fkkthlphtw kqpdhpnriv dlaaegvdpk eplpesfdwr ehgavtkvkt eghcaacwaf svtgniegqw flakkklvsl saqqlldcdv vdegcnggfp ldaykeivrm gglepedkyp yeakaeqcrl vpsdiavyin gsvelphdee kmrawlvkkg pisigitvdd iqfykggvsr pttcrlssmi hgallvgygv eknipywiik nswgpnwged gyyrmvrgen acrinrfpts avvl
```

An exemplary Tci-APY-1 sequence is deposited under the accession number CBW38507 and comprises the sequence given below as SEQ ID NO: 6.

```
                                       SEQ ID NO: 6
mllyilslvl lidalppgyp dgkehgsrpt irslpdgste ykllivtdmd kdskagewtw ravtregrlt lspdmahvsi awdensernl tssmnikgra melsdlsvfh nriltpddrt gliseiknnk mipwvflnsg pgnttspfkc ewmtikddvl yvgghgnefr nkqgeivhrn nlwiktvtpe gevtnvdwtd vfnnlrnavg isepgylthe avqwsekqgh wyflprkesk tvyveeddek kgtdlliign pdldqfetkr igvlrpergy safdfipgtd dkiivalksk evtdeptety vtvftidgei llddqkldgn ykfeglyfi
```

An exemplary Tci-MEP-1 sequence is given below as SEQ ID NO: 7.

```
                                       SEQ ID NO: 7
mrlavlllylvvsaqaglldkvkdffkggnfgektktatlskfkklfek tgilslgnklaemrskvmkklelskakkaevdrklkeveermdntvenl kdtifeinavknvgeslfqsdillltkrqveevmdgveggrpkrqafkdq nypnttwqqgvfyrfddsadyytrkvfemgtkqweeatcidfkedkekk aensiilikedgcwsyvgqvggeqplslgdgceqvgiathelghalglf htmsrydrddfitvvlenvvegfvdqyiketpqtttnygftydygsimh ygassashnnkptmvandtryqesmgsqiisfidksmindhynckadcp katsakcqnggfphprkcsecicpsgyggalcdqrptgcgqtlkakesk qflidklgfpsgvrdeftfcnhwieapegkkielkinsishgyahdgci
```

-continued
```
lggveiktsedqtrtgfrfcspndrntvlvsasnrvpiitfnrsgqgqi ileykvvs
```

An exemplary Tci-ES20 sequence is given below as SEQ ID NO: 8.

```
                                       SEQ ID NO: 8
mlrsillilvsasvyvsvqgqgngdmkkvelymgyakkdmekvreflkl kderltkllsdlfryldkttfewmkdeatleqfiqtrgkfssalvhpdv qkrykdnrklwafryarlmnciggsdmgrataylpgvsvqekeetlrys lklertcaytyfr
```

As such, one embodiment of this invention provides one or more of the *T. circumcincta* antigens selected from the group consisting of (i)-(ix) above or comprising one or more of the sequences provided as SEQ ID NOS: 1-8 (or a fragment thereof), for raising immune responses in animals—in particular ovine animals such as sheep and goats.

Advantageously, the invention provides vaccine compositions comprising one or more of the antigens provided as (i)-(ix) above, or one or more antigens comprising the sequences provided as SEQ ID NOS: 1-8 (or a fragment thereof), for use in raising immune responses (for example protective immune responses) in ovine animals.

SEQ ID NOS: 1-8 above (and any fragments, variants or derivatives thereof), may be regarded as reference sequences—against which the sequences of the fragments, variants and derivatives described herein are compared. In other embodiments, the reference sequences may be the wild-type sequences of any of the antigens given as (i)-(viii)

In addition to the definition provided above, the term "antigen" also encompasses fragments of any of the antigens described herein—this includes fragments of the antigens listed as (i)-(viii) above and antigens encoded by sequences comprising parts of SEQ ID NOS: 1-8. In particular, the term "antigen" encompasses antigenic or immunogenic fragments or epitopes capable of eliciting an immune response in an animal. Advantageously, the antigen fragments described herein are capable of eliciting an immune response which is substantially identical or similar to, an immune response elicited by the complete antigen from which the fragment is derived. In one embodiment, the antigen fragments provided by this invention are capable of providing protective immune responses against *T. circumcincta* in ovine animals.

In other embodiments, the term "antigen" or "antigen fragment" may encompass variants or derivatives of any of the antigen(s) described herein—such antigens being referred to as "variant" or "derivative" antigens. Again, it should be understood that these terms include variants/derivatives of any of the antigens given as (i)-(ix) above or encoded by any of SEQ ID NOS: 1-8. Further, the skilled man would understand that any variant or derivative antigen may elicit an immune response in an ovine animal similar or substantially identical to an immune response elicited by the corresponding complete or native antigen in the same host—such variants/derivatives may be referred to as "immunogenic variants/derivatives". An immunogenic variant/derivative may comprise or be encoded by, a protein/peptide sequence or nucleic acid or amino acid sequence which comprises one or more nucleobase and/or amino acid substitutions, inversions, additions and/or deletions relative to a reference sequence.

One of skill will appreciate that the term "substitution" may encompass one or more conservative substitution(s). One of skill in this field will understand that the term "conservative substitution" is intended to embrace the act of replacing one or more amino acids of a protein or peptide with an alternate amino acid with similar properties and which does not substantially alter the physico-chemical properties and/or structure or function of the native (or wild type) protein.

In the context of this invention, a variant/derivative antigen may comprise or be encoded by a mutant sequence which when compared to a reference sequence (such as for example a wild type sequence (including sequences encoding any of the specific *Teladorsagia* antigens given as (i)-(viii) above) or sequences comprising SEQ ID NOS: 1-8 (or fragments thereof) above), is found to contain one or more amino acid/nucleotide substitutions, additions, deletions and/or inversions.

An antigen which may be regarded as a derivative may further comprise one or more features of a fragment or variant described herein optionally in combination with one or more modifications to the structure of the antigen or one or more of the amino acid residues thereof.

The fragments, mutants, variants and/or derivatives provided by this invention may comprise anything from about 5 to about 10 residues (amino acids and/or nucleic acids) of the complete amino acid or nucleic acid sequence (n) of (or encoding) the complete wild-type or native *Teladorsagia* (for example *T. circumcincta*) antigen, to about n−1 residues. In certain embodiments, the fragments, variants and/or derivatives provided by this invention comprise at least about 10, 15, 20, 25, 30, 35, 40, 45, 50, 75, 100, 150, 200, 250, 300 residues—the upper limit (n−1) depending upon the size (n) of the nucleic acid encoding the complete antigen or the number (n) of amino acid residues comprising the primary sequence of the antigen.

Additionally, or alternatively, the fragments, variants and/or derivatives provided by this invention are at least 30%, 35%, 40%, 45%, 50%, 55%, 60%, 65%, 70%, 75%, 80%, 85%, 90%, 95%, 96%, 97%, 98%, 99% homologous or identical to the various reference sequences provided herein.

The degree of (or percentage) "homology" between two or more (amino acid or nucleic acid) sequences may be determined by aligning two or more sequences and determining the number of aligned residues which are identical or which are not identical but which differ by redundant nucleotide substitutions (the redundant nucleotide substitution having no effect upon the amino acid encoded by a particular codon, or conservative amino acid substitutions.

A degree (or percentage) "identity" between two or more (amino acid or nucleic acid) sequences may also be determined by aligning the sequences and ascertaining the number of exact residue matches between the aligned sequences and dividing this number by the number of total residues compared—multiplying the resultant figure by 100 would yield the percentage identity between the sequences.

In one embodiment, the invention provides multi-component compositions and vaccines for use in raising an immune response in an animal, the vaccine and/or composition comprising, consisting or substantially consisting of, each of the following *T. circumcincta* antigens:

(i) calcium-dependent apyrase-1 (Tci-APY-1);
(ii) astacin-like metalloproteinase-1 (Tci-MEP-1);
(iii) excretory/secretory protein (unknown function: Tci-ES20);
(iv) cathepsin F-1 (Tci-CF-1);
(v) transforming growth protein 2-like protein (a TGFβ homologue: Tci-TGH-2);
(vi) activation associated secretory protein (Tci-ASP-1);
(vii) macrophage migration inhibitory factor (Tci-MIF-1); and
(viii) surface associated antigen (Tci-SAA-1).

In one embodiment, one or more of the *T. circumcincta* antigens provided as (i)-(viii) above, is/are provided as a fragment or variant/derivative (as defined above).

The inventors have discovered that animals (in particular sheep) administered a vaccine composition comprising eight separate *T. circumcincta* antigens (for example, the antigens given as (i)-(viii) above) develop an immune response which confers a level of protection which is far higher than that observed following exposure to prior art vaccines and vaccine compositions. For example, the vaccines provided by this invention have been observed to reduce host FECs and luminal parasite burdens by approximately 10%-90%, 15%-85%, 20%-80%, 25%-75% or 30%-70%.

Without wishing to be bound by theory, the inventors hypothesis that the success of the vaccines and vaccine compositions described herein is due to the use of antigens which elicit an immune response which mimics that occurring during a natural infection and which serves to prevent or suppress nematode-derived immunomodulation.

Antigens to be exploited in this invention may be obtained using recombinant technology. In one embodiment, an expression vector comprising one or more nucleic acid sequences encoding a *T. circumcincta* antigen (such as any of those described herein) may be used to produce one or more recombinant *T. circumcincta* antigens for use in raising immune responses in animals—particularly ovine animals.

Protocols for the recombinant preparation of any of the antigens provided by this invention are described herein— see for example section entitled "Production of recombinant proteins for immunisation". Nevertheless, one of skill will appreciate that other methods (for example methods utilising different primers and vectors etc.) may also be used.

In view of the above, the invention provides vectors, for example expression vectors, comprising nucleic acid sequence(s) encoding one or more of the *T. circumcincta* antigens described herein (or fragments thereof). By way of example, the vectors provided by this invention may comprise plasmid expression systems such as those known as pET, pPICZ, pSUMO and/or pGST. Vectors according to this invention may otherwise be referred to as "nucleic acid constructs".

In a further aspect, the present invention provides host cells transfected or transformed with a vector as described herein. Eukaryotic or prokaryotic cells, such as, for example plant, insect, mammalian, fungal and/or bacterial cells, may be transfected with one or more of the vectors described herein. One of skill in this field will be familiar with the techniques used to introduce heterologous or foreign nucleic acid sequences, such as expression vectors, into cells and these may include, for example, heat-shock treatment, use of one or more chemicals (such as calcium phosphate) to induce transformation/transfection, the use of viral carriers, microinjection and/or techniques such as electroporation. Further information regarding transformation/transfection techniques may be found in Current Protocols in Molecular Biology, Ausuble, F. M., ea., John Wiley & Sons, N.Y. (1989) which is incorporated herein by reference.

In one embodiment, the host cell is a bacterial cell such as, for example, an *Escherichia coli* cell.

In view of the above, the present invention further provides a process for the production of a recombinant *Tela-*

*dorsagia* antigen encoded by any of the sequences described herein (or an immunogenic fragment thereof), which recombinant antigen (or immunogenic fragment thereof) is for use in raising an immune response in an animal (for example an ovine), said method comprising the step of (a) transforming a host cell with a nucleic acid sequence according to this invention (e.g. a nucleic acid encoding a *T. circumcincta* antigen) or transfecting a host cell with a nucleic acid construct of the invention; (b) culturing the cells obtained in (a) under conditions in which expression of the nucleic acid (or rather a protein encoded thereby) takes place; and (c) isolating the expressed recombinant protein or peptide from the cell culture and/or the culture supernatant.

Recombinant proteins/peptides produced according to the method described above may be partially purified from the host cell before being used in a vaccine or vaccine composition. Where the polypeptide is secreted from the host cell, the cells may be separated from the media by centrifugation. In such a situation, the supernatant, which contains the secreted polypeptide, may be used directly as a vaccine, or in a vaccine composition. Alternatively, the polypeptide may be partially purified from this supernatant, for example using affinity chromatography.

In one embodiment, the invention provides a composition (for example a vaccine composition) comprising, consisting or substantially consisting of, each of the following recombinant *T. circumcincta* antigens:
 (i) calcium-dependent apyrase-1 (Tci-APY-1);
 (ii) astacin-like metalloproteinase-1 (Tci-MEP-1);
 (iii) excretory/secretory protein (unknown function: Tci-ES20);
 (iv) cathepsin F-1 (Tci-CF-1);
 (v) transforming growth protein 2-like protein (a TGFβ homologue: Tci-TGH-2);
 (vi) activation associated secretory protein (Tci-ASP-1);
 (vii) macrophage migration inhibitory factor (Tci-MIF-1); and
 (viii) surface associated antigen (Tci-SAA-1);
for use in raising an immune response in an animal (for example an ovine species—including sheep and goats).

In one embodiment, any of the *Teladorsagia* antigens described herein may be admixed with another component, such as another polypeptide and/or an adjuvant, diluent or excipient. In one embodiment, the vaccine compositions provided by this invention may comprise a QuilA adjuvant. Additionally, or alternatively, vaccines or vaccine compositions provided by this invention may, for example, contain viral, fungal, bacterial or other parasite antigens used to control other diseases/infections or infestations. For example, the vaccine or vaccine composition may be included within a multivalent vaccine, which includes antigens against other ovine (for example, sheep) diseases.

In a still further aspect, the present invention provides an ovine population, for example a farmed population of sheep and/or goats, treated, vaccinated or immunised with a vaccine or composition described herein, said vaccine or composition comprising one or more of the *Teladorsagia* antigens described herein.

One of skill will appreciate that the vaccines described in this invention may take the form of subunit-type vaccines whereby one or more *Teladorsagia* antigens are used to inoculate an animal. Additionally or alternatively, the vaccine may comprise a nucleic acid molecule (known as a DNA vaccine) encoding one or more antigens encoded by SEQ ID NOS: 1-8 above or an immunogenic fragment thereof, to be expressed by the cells of an animal to be vaccinated. In this way, constitutive expression of *Telador-* *sagia* antigens in a vaccinated host (such as, for example a vaccinated ovine subject (sheep or goat)) may elicit a constitutive protective immune response.

The compositions, including the vaccine compositions, provided by this invention may be formulated as sterile pharmaceutical compositions comprising one or more of the antigens described herein and a pharmaceutical excipient, carrier or diluent. These composition may be formulated for oral, topical (including dermal and sublingual), parenteral (including subcutaneous, intradermal, intramuscular and intravenous), transdermal and/or mucosal administration.

The (vaccine) compositions described herein, may comprise a discrete dosage unit and may be prepared by any of the methods well known in the art of pharmacy. Methods typically include the step of bringing into association one or more of the *T. circumcincta* antigens described herein with liquid carriers or finely divided solid carriers or both.

Compositions (the term "composition" including a vaccine compositions), suitable for oral administration wherein the carrier is a solid are most preferably presented as unit dose formulations such as boluses, capsules or tablets each containing a predetermined amount of one or more of the *Teladorsagia* antigens of this invention. A tablet may be made by compression or moulding, optionally with one or more accessory ingredients. Compressed tablets may be prepared by compressing in a suitable machine an active compound (for example one or more *T. circumcincta* antigen(s)) in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersible granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Compositions suitable for oral administration include controlled release dosage forms, e.g., tablets wherein an active compound (for example one or more *Teladorsagia* antigens) is formulated in an appropriate release-controlling matrix, or is coated with a suitable release-controlling film. Such compositions may be particularly convenient for prophylactic use.

Composition and vaccine compositions formulated for parenteral administration include sterile solutions or suspensions of an active compound (for example one or more *Teladorsagia* antigens) in aqueous or oleaginous vehicles.

Injectable compositions and vaccines may be adapted for bolus injection or continuous infusion. Such preparations are conveniently presented in unit dose or multi-dose containers, which are sealed after introduction of the formulation until required for use. Alternatively, an active compound (for example one or more *T. circumcincta* antigens) may be in powder form that is constituted with a suitable vehicle, such as sterile, pyrogen-free water or PBS before use.

Compositions comprising one or more *Teladorsagia* antigens may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. They may also include preparations or adjuvants known to enhance the affinity and/or longevity of an animal (for example ovine) immune response, such as single or double emulsions of oil in water. Such long-acting compositions are particularly convenient for prophylactic use.

Compositions suitable (or formulated) for mucosal administration include compositions comprising particles for aerosol dispersion, or dispensed in drinking water. When dispensed such compositions should desirably have a particle diameter in the range 10 to 200 microns to enable retention in, for example, the nasal cavity; this may be achieved by, as appropriate, use of a powder of a suitable particle size or choice of an appropriate valve. Other suitable compositions include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

It should be understood that in addition to the carrier ingredients mentioned above, the various compositions described herein may Include, an appropriate one or more additional (pharmaceutically acceptable) carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

Pharmaceutically acceptable carriers are well known to those skilled in the art and include, but are not limited to, 0.1 M and preferably 0.05 M phosphate buffer or 0.8% saline. Additionally, pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Compositions suitable for topical formulation may be provided for example as gels, creams or ointments.

Compositions for veterinary use may conveniently be in either powder or liquid concentrate form. In accordance with standard veterinary formulation practice, conventional water-soluble excipients, such as lactose or sucrose, may be incorporated in the powders to improve their physical properties. Thus, particularly suitable powders of this invention comprise 50 to 100% w/w and preferably 60 to 80% w/w of the active ingredient(s) (for example one or more *T. circumcincta* antigens) and 0 to 50% w/w and preferably 20 to 40% w/w of conventional veterinary excipients. These powders may either be added to, for example, animal feed—perhaps by way of an intermediate premix, or diluted in animal drinking water.

Liquid concentrates of this invention suitably contain one or more *T. circumcincta* antigens and may optionally further include an acceptable water-miscible solvent for veterinary use, for example polyethylene glycol, propylene glycol, glycerol, glycerol formal or such a solvent mixed with up to 30% v/v of ethanol. The liquid concentrates may be administered to the drinking water of animals.

In general, a suitable dose of each the *T. circumcincta* antigens provided by this invention may be in the range of about 10 to about 100 µg protein per animal. Furthermore, the one or more antigens described herein may be administered on about 2 to about 5 occasions over a period of about 1 to about 10 weeks or on an annual boost basis. In one embodiment, each animal may be administered about 10, 15, 20, 25, 30, 35, 40, 45, 50, 55, 60, 65, 70, 75, 80, 85, 90, 95 or 100 g of each (or a predetermined selection of) the one or more antigens described herein. As such, where the vaccine comprises 8 antigens, the total protein content may range from about 80 µg to about 800 µg. Furthermore, each animal may be administered the antigen(s) on 2, 3, 4 or 5 occasions over a 1, 2, 3, 4, 5, 6, 7, 8, 9 or 10 week period. It should be understood that each animal may receive the same or a different dose of the *T. circumcincta* antigen(s) on each administration occasion.

In one embodiment, a vaccine formulated for administration to sheep may comprise approximately 50 µg of each *Teladorsagia* (for example *T. circumcincta*) antigen. As such, where the vaccine comprises, for example, 8 *T. circumcincta* antigens, the total protein (antigen) content may be in the region of 400 µg. Further, the vaccine may be administered three times with a three week gap between each administration.

In addition to providing *T. circumcincta* antigens for use in raising immune responses in animals, the present invention may also provide polyclonal and/or monoclonal antibodies (or antigen binding fragments thereof) that bind (or have affinity or specificity for) any of the *Teladorsagia* antigens provided by this invention. Production and isolation of polyclonal/monoclonal antibodies specific for protein/peptide sequences is routine in the art, and further information can be found in, for example "Basic methods in Antibody production and characterisation" Howard & Bethell, 2000, Taylor & Francis Ltd. Such antibodies may be used in diagnostic procedures, to, for example detect or diagnose *T. circumcincta* infection/infestations in animal (for example ovine) species, as well as for passive immunisation.

The present invention further provides a vaccine for use in preventing or controlling *T. circumcincta* infection/infestation and associated diseases in ovine hosts. The vaccine may be a polypeptide or polynucleotide vaccine.

The invention further provides a method for immunizing an ovine subject against *T. circumcincta* infection/infestation and associated disease (for example secondary infections etc.), said method comprising the step of administering a vaccine of the invention to the ovine subject.

While this invention predominately concerns antigens derived from the nematode organism *T. circumcincta* and their use in vaccine compositions for raising immune responses in animals (particularly ovine animals), owing to a high degree of homology between the *T. circumcincta* antigens described herein and specific antigens from other, closely related, nematode species, the utility of the antigens provided by this invention is not necessarily limited to raising immune responses which are protective against *Teladorsagia* infections/infestations. In particular, the antigens described herein exhibit significant homology/identity to certain antigens derived from the bovine pathogen, *Ostertagia ostertagi*. Details of these antigens and an indication of the level of identity exhibited between the disclosed *T. circumcinta* antigens and certain related *O. ostertagi* antigens are given in the table below.

| Teladorsagia circumcincta Antigen | Accession number | Function* | Closest Ostertagia ostertagi homologue | % identity | % Coverage | O. ost reference |
|---|---|---|---|---|---|---|
| Tci-SAA-1 | CAQ43040 | L3-enriched surface associated antigen | BQ098696.1[a,b] | 94% | 100% (aa1-162) | Unpublished |
| Tci-MIF-1 | CBI68362 | L3-enriched macrophage migration inhibitory factor | BQ457770.1[a] | 99% | 91% (aa11-115) | Unpublished |
| Tci-ASP-1 | CBJ15404 | L4-enriched activation-associated secretory protein | CAD23183.1 | 76% | 97% (aa5-235) | Mol Biochem Parasitol 2003; 126, 201-208 |
| Tci-TGH-2 | ACR27078 | Transforming growth protein 2-like protein | No significant hit in NCBI, EMBL or Nembase 4 | — | — | — |
| Tci-CF-1 | ABA01328** | L4-enriched Secreted cathepsin F | BQ457843.1[a] | 73% | 59% (aa12-229) | Unpublished |
| Tci-ES20 | Not yet submitted*** | Excretory/secretory (ES) protein | CAC44259.1 | 35% | 100% (aa1-140) | Mol Biochem Parasitol 2003; 126, 201-208 |
| Tci-MEP-1 | Not yet submitted*** | Astacin-like ES metalloproteinase | CAD19995.2 | 69% | 100% (aa1-498) | Parasitology 2002; 125, 383-391 |
| Tci-APY-1 | CBW38507 | L4-enriched ES calcium-activated apyrase | ADG63133.1 | 92% | 96% (aa12-339) | Parasitology 2011; 138, 333-343 |

*Putative or inferred function
**Tci-CF-1 is highly polymorphic, the clone used for vaccine production had following amino acid substitutions compared to published sequence. In each case the amino acid in the published sequence is in italics, that in the vaccine isoform sequence is in normal font and the amino acid position in the published sequence is in subscript: $I_{44} \Rightarrow T_{44}$, $N_{101} \Rightarrow D_{101}$, $T_{129} \Rightarrow A_{129}$, $R_{137} \Rightarrow Q_{137}$, $R_{305} \Rightarrow K_{305}$, $L_{306} \Rightarrow P_{306}$, $S_{307} \Rightarrow Y_{307}$
***Full length sequences not yet deposited.
[a]From translated EST sequence
[b]with following caveat from authors: "WARNING: Subsequent examination of these samples has revealed the presence of an additional Trichostrongyloidea cattle nematode, *Cooperia oncophora*.
Sequences in this library may derive from either *Ostertagia* or *Cooperia*."

In view of the above, it should be understood that the various aspects and embodiments of this invention (as applying to *T. circumcincta* antigens and their use in raising immune responses in animals, especially ovines) may further apply to one or more of the *O. ostertagi* antigens described above.

Moreover, in view of the levels of identity exhibited between the *T. circumcincta* antigens described herein and the *O. ostertagi* antigens identified above, one or more of the *T. circumcincta* antigens described herein may be used to raise immune responses in bovine subjects, the immune responses being protective and serving to reduce, prevent, treat or eliminate *Ostertagia* (for example *O. ostertagi*) infections/infestations. One of skill will appreciate that the *T. circumcincta* antigens provided by this invention may be used individually or together (for example 2, 3, 4, 5, 6, 7 or all 8 of the *T. circumcincta* antigens) to raise immune responses in bovine hosts.

Alternatively, the present invention may extend to the use of one or more (for example 2, 3, 4, 5, 6 or all 7) of the *O. ostertagi* antigens presented in the table above, optionally in combination with one or more of the *T. circumcincta* antigens described herein, for use in raising immune responses in bovine subjects. Again, such immune responses may be protective against *Ostertagia* infections/infestations.

In one embodiment, this invention extends to compositions or vaccine compositions comprising one or more of the *Ostertagia* antigens described above optionally in combination with one or more the *T. circumcincta* antigens described herein, for use in raising immune responses in bovine subjects.

The invention may further provide uses of one or more of the *Ostertagia* antigens optionally in combination with one or more of the *Teladorsagia* antigens for the manufacture of medicaments for use in the treatment and/or prevention of an infection/colonisation by/with an *Ostertagia* pathogen in a bovine host. Similarly, the invention may also embrace methods of raising anti-*Ostertagia* responses in bovine hosts, the methods comprising administering to a bovine subject, an amount of one or more of the *Ostertagia* antigens described above, sufficient to induce an anti-*Ostertagia* immune response.

One of skill will appreciate that references to the *Ostertagia* antigens described above not only include antigens comprising or consisting of the sequences identified by the Accession numbers presented in the table above, but fragments thereof—in particular, fragments which are capable of raising immune responses (for example protective immune responses) in bovine animals (i.e. the fragments are antigenic and/or immunogenic) as well as mutants, variants and/or derivatives thereof. It should be understood that the definitions of fragments, mutants, variants and/or derivatives provided in relation to the *Teladorsagia* antigens of this invention, also apply to the *Ostertagia* antigens described above. As such, the *Ostetagia* antigen fragments, variants and/or derivatives encompassed by this invention may exhibit at least 30%, 35%, 40%, 45%, 50%, 55%, 60%, 65%, 70%, 75%, 80%, 85%, 90%, 95%, 96%, 97%, 98%, 99% homology or identity to the various *Ostertagia* sequences described above.

DETAILED DESCRIPTION

Figure 1B:
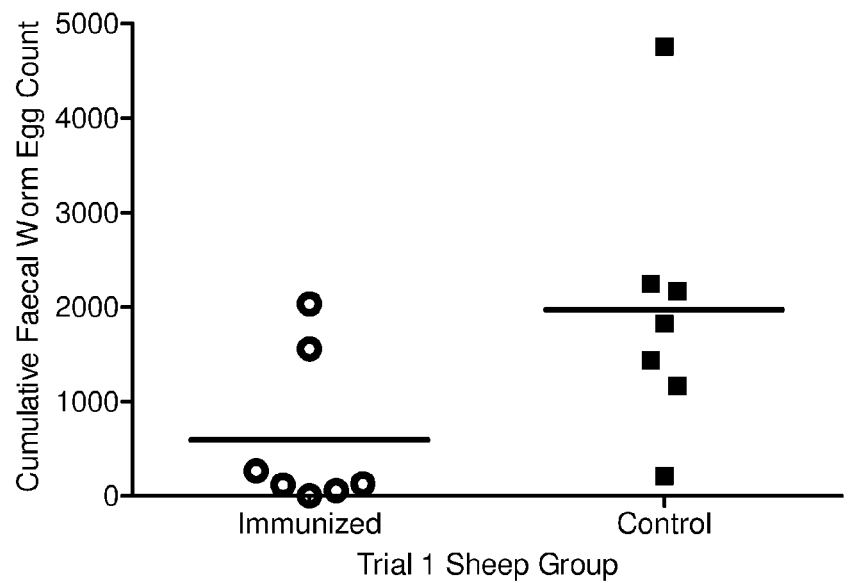
Figure 1C:
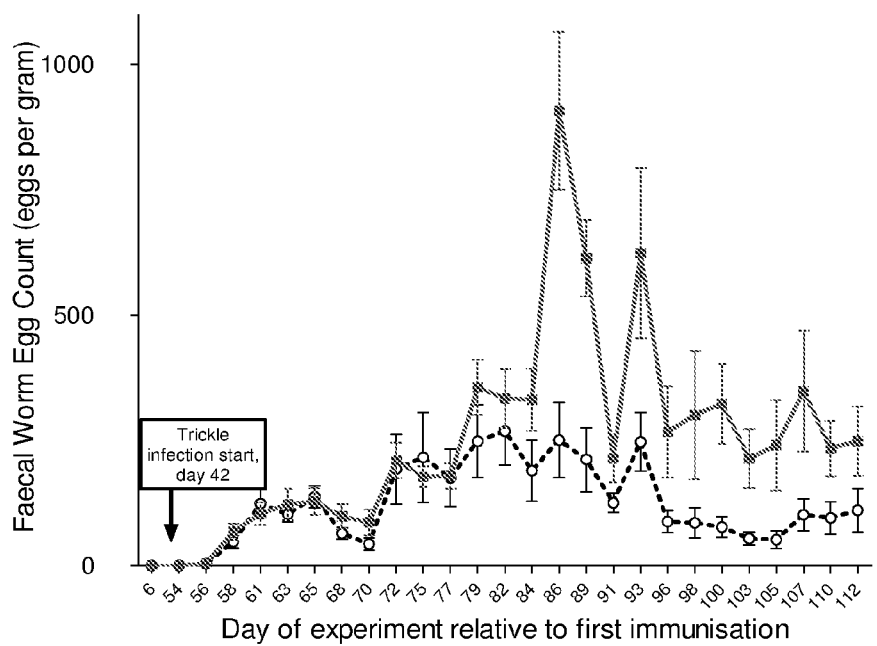
Figure 1D:
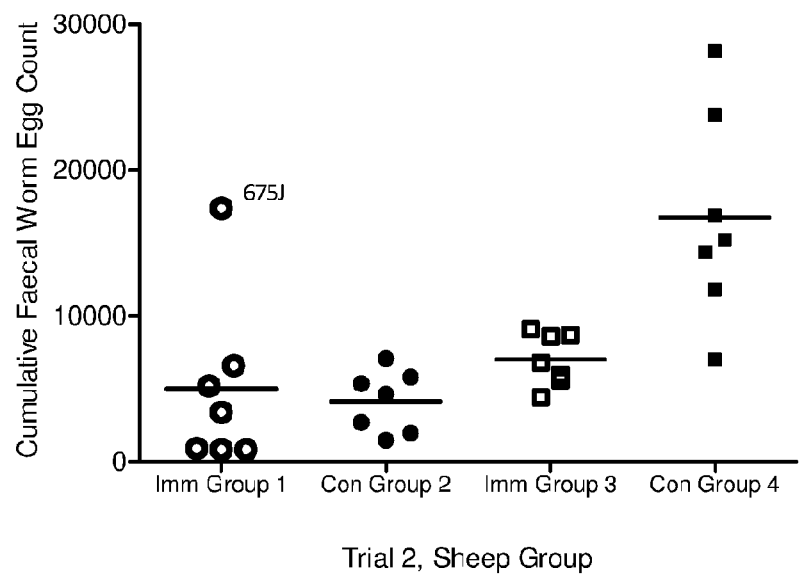

The present invention will now be described in detail with reference to the following Figures which show:

FIGS. 1A-1D: Effects of immunization of sheep with recombinant antigens derived from *Teladorsagia circumcincta* on faecal worm egg counts (FWEC) after challenge infection. FIGS. 1A and 1C: FWECs of sheep challenged with 2000 *T. circumcincta* three times per week for 4 weeks following immunization with an 8-protein cocktail in the context of Quil A (dashed line) or with Quil A only (solid line). Each data point represents the arithmetic mean FWEC±SEM. FIG. 1A represents data from Trial 1; FIG. 1C represents data from Trial 2. FIGS. 1B and 1D show cumulative FWECs, for each animal in each group in Trial 1 (FIG. 1B) and Trial 2 (FIG. 1D). "Imm" represents sheep immunized with the 8-protein cocktail; "Con" represents those administered with Quil A adjuvant only. Note that, in FIG. 1D, for Groups 1 and 2 in Trial 2, cumulative FWEC is calculated over 84 days, whereas for Groups 3 and 4 cumulative FWEC is calculated over 112 days. One "outlier" animal in Group 1 of Trial 2, sheep number 675J, is indicated.

Figure 2:
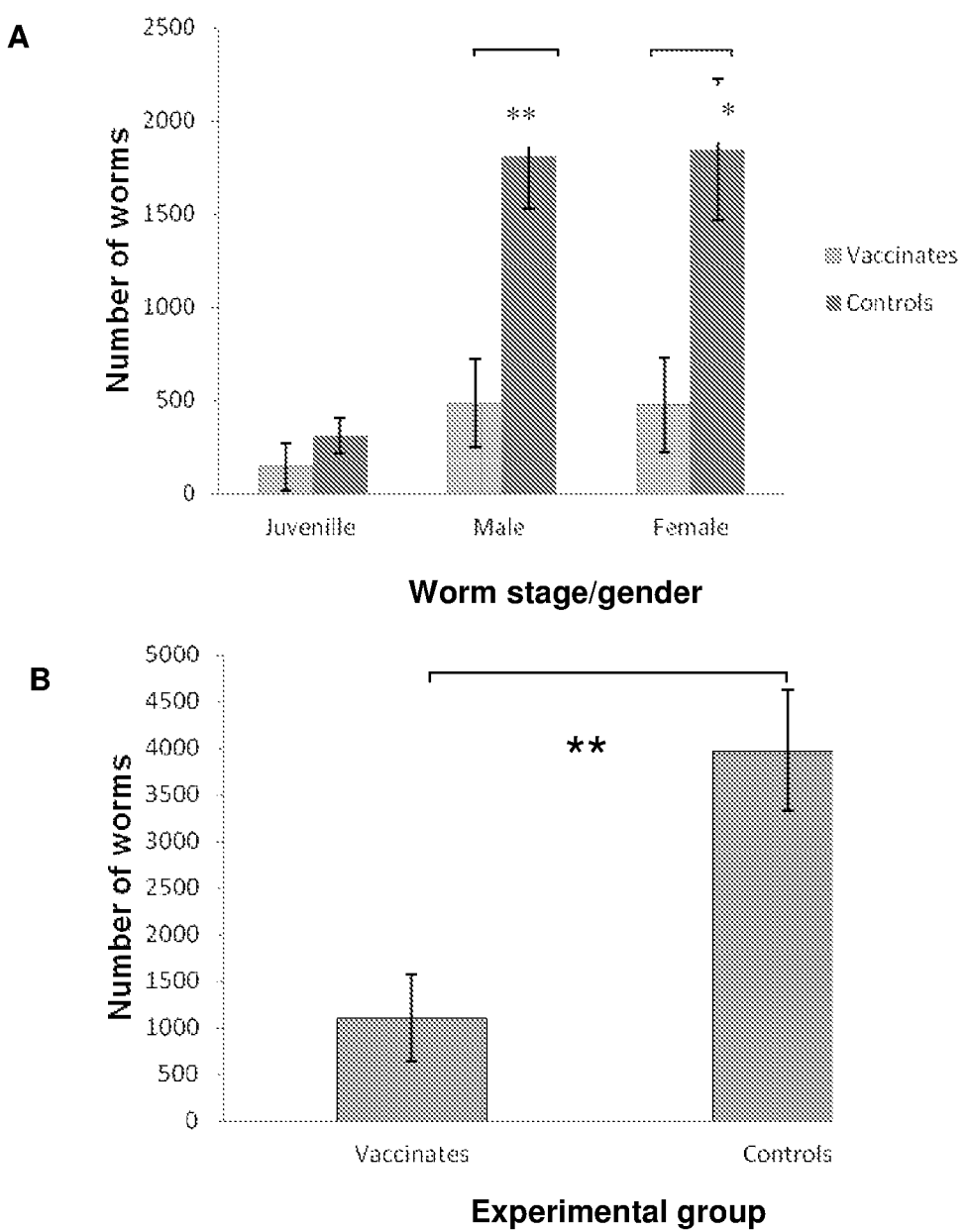

FIG. 2. Trial 1: Lumenal *T. circumcincta* burdens of sheep in Group 1 and Group 2. Each data point represents the mean number (±SEM) of *T. circumcincta* enumerated in lumenal contents of seven sheep in each group. Panel A depicts counts categorized into developmental stage and the gender of the adult worms harvested. Panel B depicts the counts as overall burdens (all stages and genders). "*" denotes a significant difference between the means ($P<0.05$), "**" denotes a highly significant difference between mean ($P<0.01$).

Figure 3:
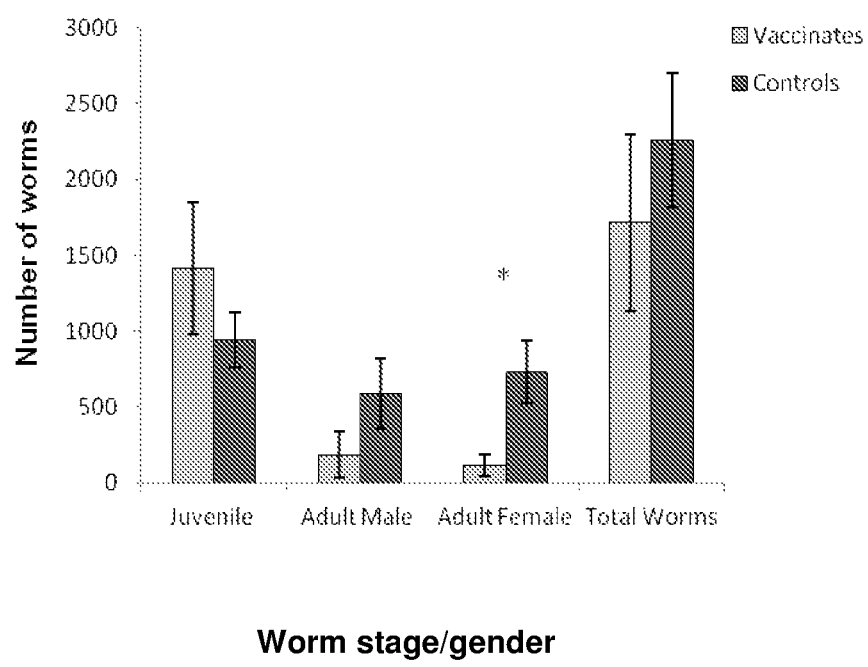

FIG. 3. Trial 1: Mucosal *T. circumcincta* burdens of sheep in Group 1 and Group 2. Each data point represents the mean number (±SEM) of nematodes harvested from the mucosal contents of seven sheep in each group. "*" denotes a significant difference between the means ($P<0.05$).

Figure 4:
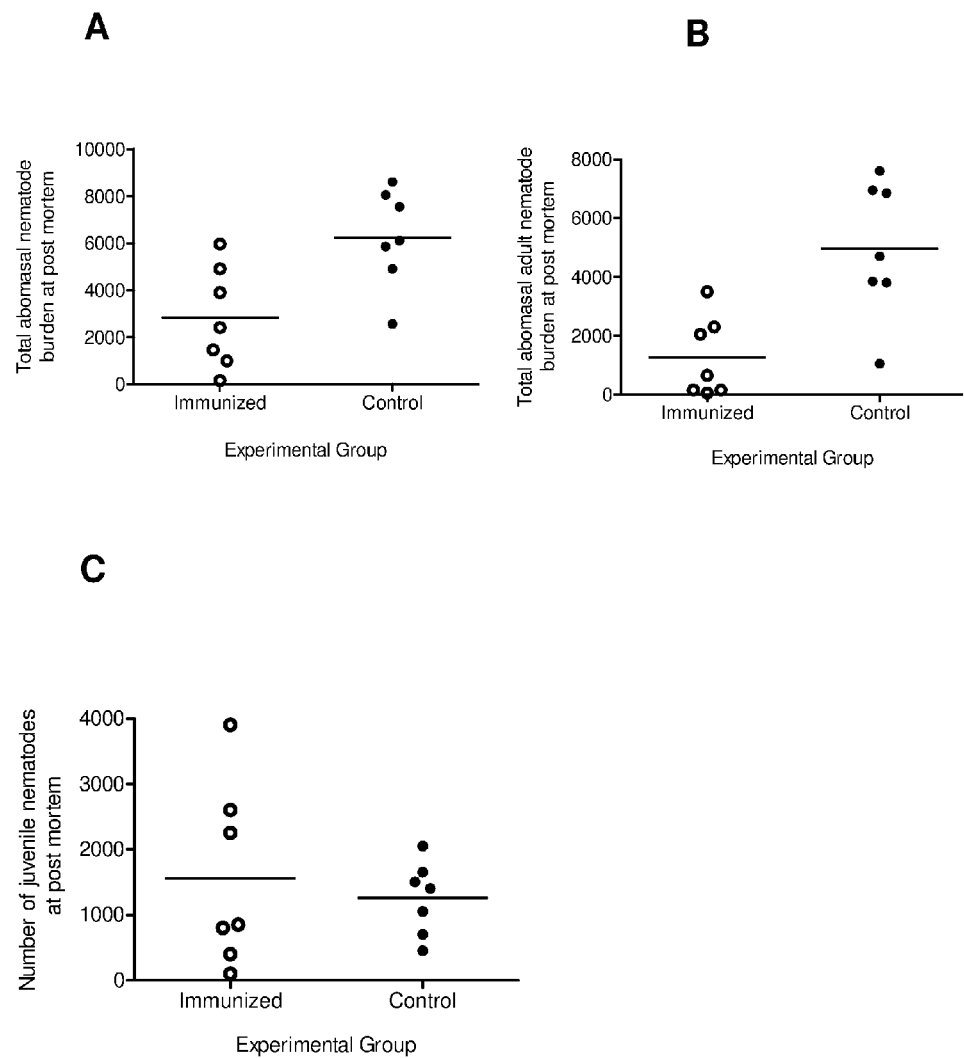

FIG. 4: Effects of immunization of sheep with recombinant antigens derived from *Teladorsagia circumcincta* on abomasal nematode burden after challenge infection (Trial 1). Panels A-C represent the number of *T. circumcincta* enumerated in the abomasum. Panel A depicts the total nematode burden, panel B the adult nematode burden and panel C the juvenile nematode burden of each of seven sheep in Group 1 (immunized) or Group 2 (control, adjuvant only). Horizontal bars represent the mean value.

Figure 5:
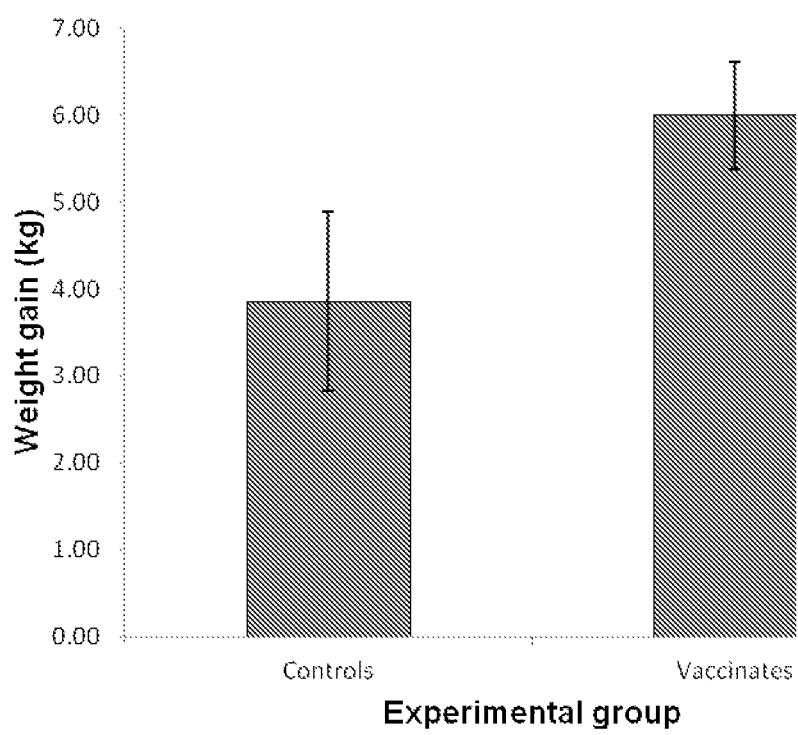

FIG. 5: Weight gain of sheep in Group 1 and Group 2 from Day 0 to Day 84 of the experiment (Trial 1).

Figure 6:
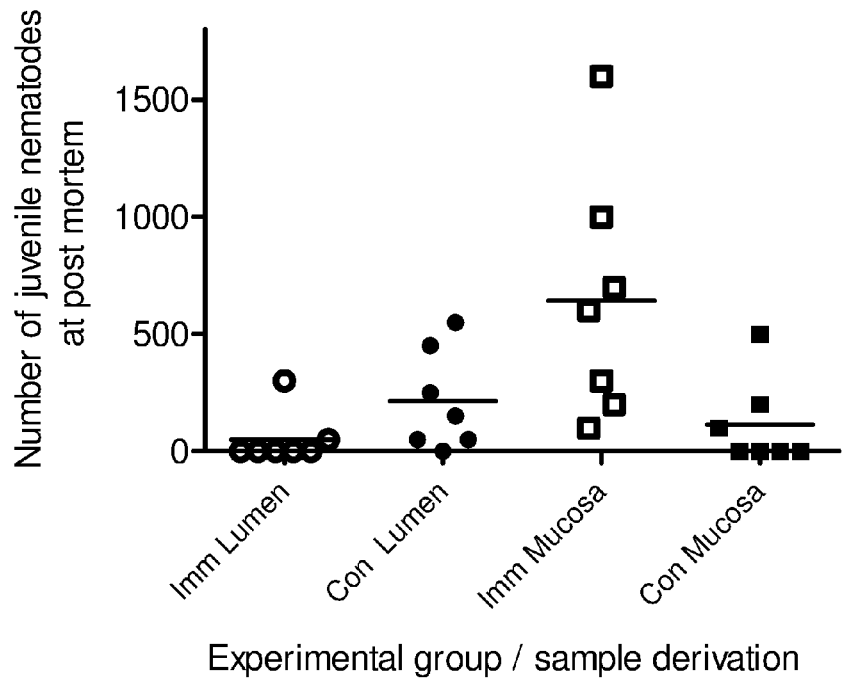

FIG. 6: Effects of immunization of sheep with recombinant antigens derived from *Teladorsagia circumcincta* on juvenile nematode burden distribution after challenge infection (Trial 2; Group 1 and Group 2). Numbers of juvenile *T. circumcincta* enumerated in the abomasal lumen and the abomasal mucosa of each of these sheep are shown. "Imm" represents sheep immunized with the 8-protein cocktail; "Con" represents those immunized with Quil A adjuvant only.

Figure 7:
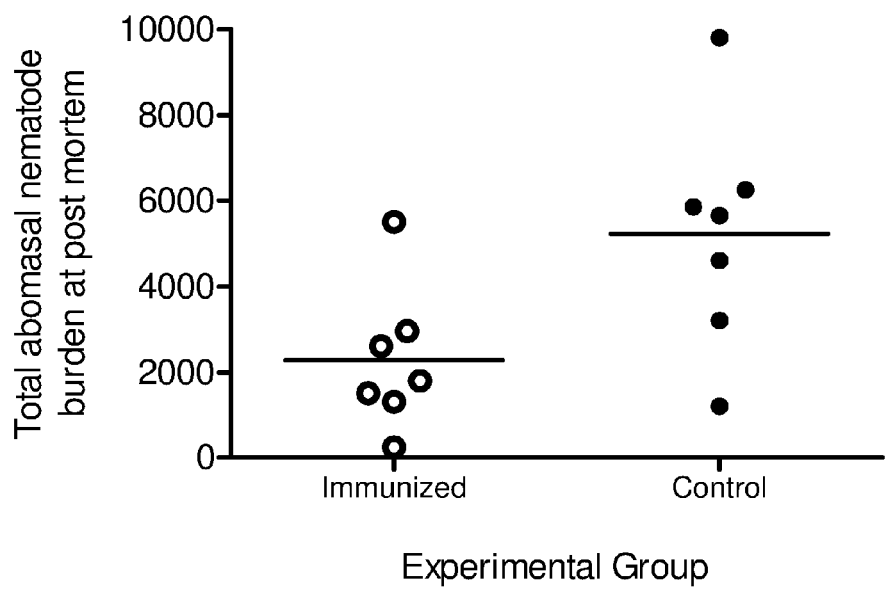

FIG. 7: Effects of immunization of sheep with recombinant antigens derived from *Teladorsagia circumcincta* on abomasal nematode burden after challenge infection (Trial 2; Group 3 and Group 4). Data shown represent the total numbers of *T. circumcincta* enumerated in the abomasum of each of seven sheep in Group 3 (immunized) or Group 4 (control, adjuvant only).

Figure 8:
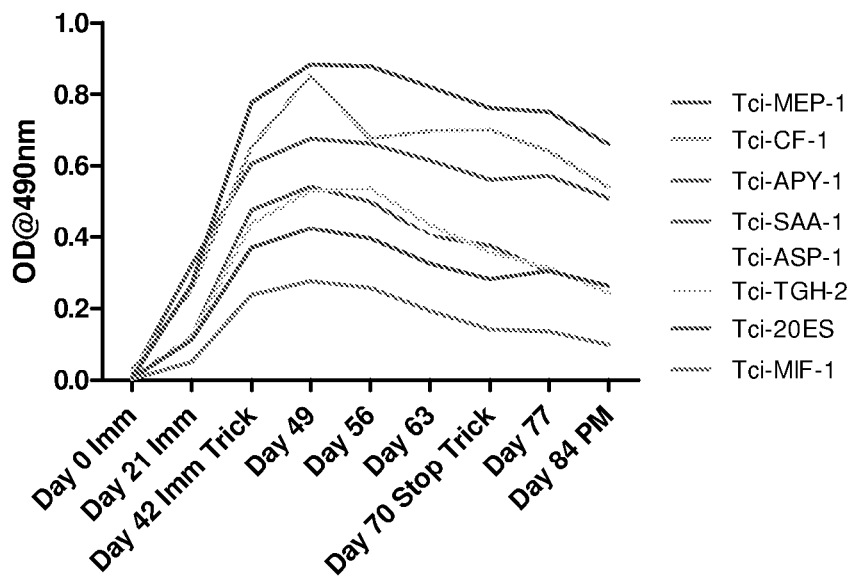
Figure 8:
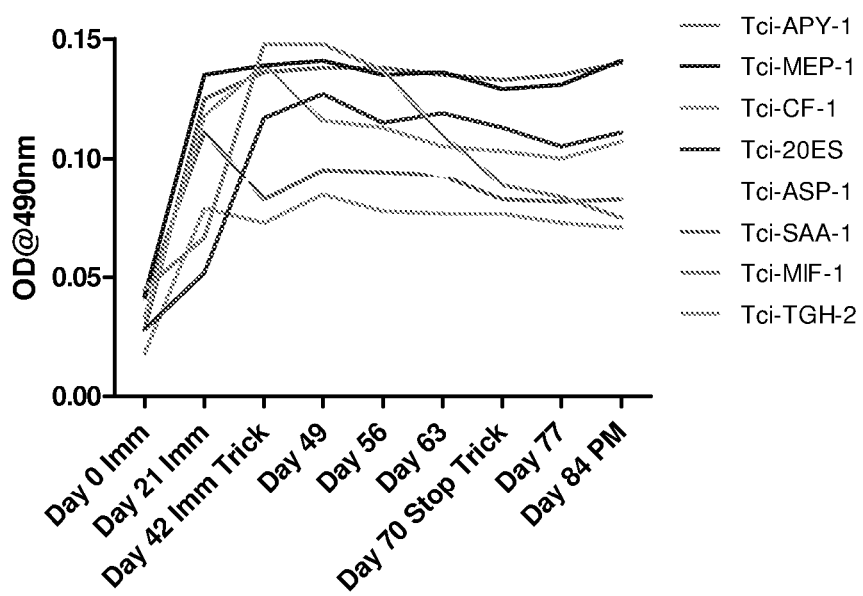

FIG. 8: Serum antibody responses of sheep to the recombinant proteins used to immunize Group 1 in Trial 1. Each data point represents the mean value derived from 7 sheep. Standard errors in panels A and B have been omitted to aid interpretation. Panels A and B show serum antibody responses for vaccinated sheep (Group 1). Panel A shows data for IgG, panel B shows data for IgA. "Imm" represents dates on which sheep were immunized; "Trick" represents the trickle infection; "PM" is the post mortem date.

Figure 9:
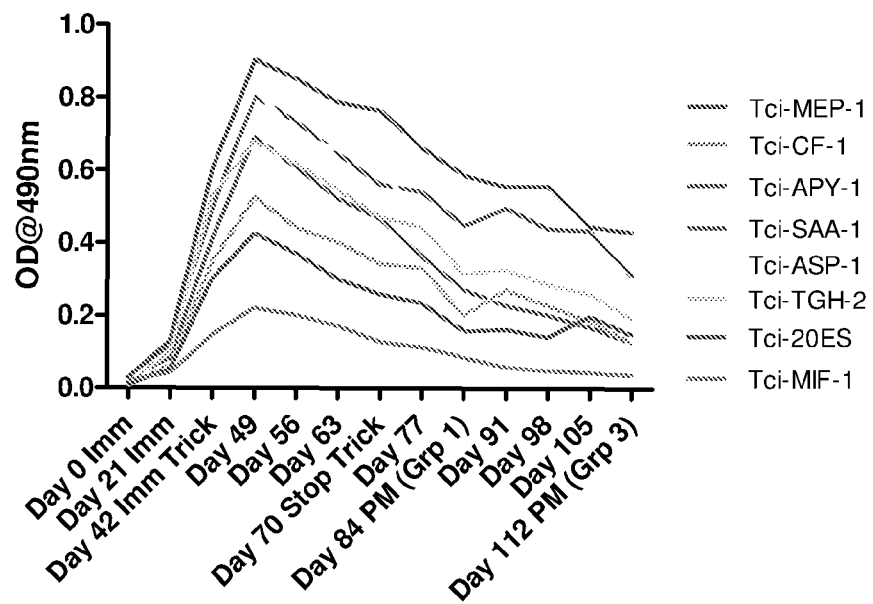
Figure 9:
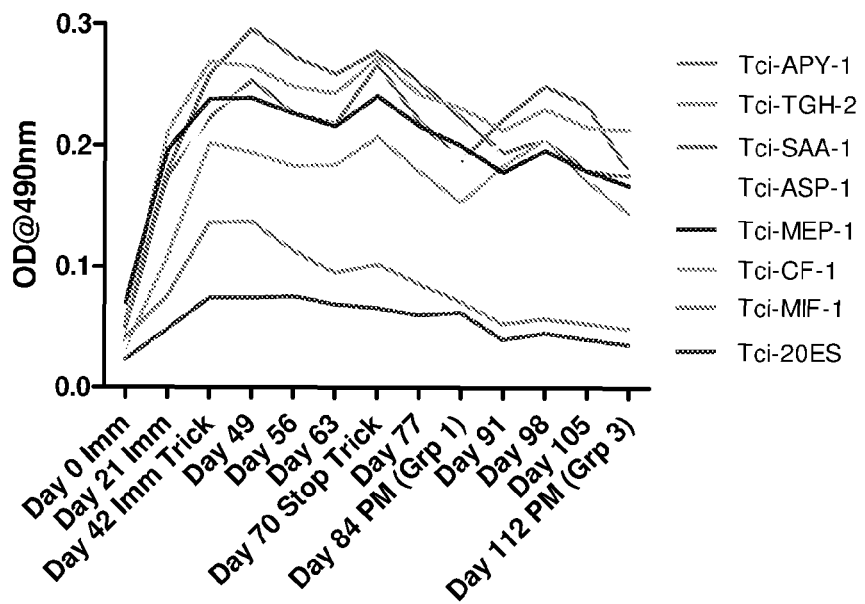

FIG. 9: Serum antibody responses of sheep to the recombinant proteins used to immunize Groups 1 and 3 in Trial 2. Each data point represents the mean value derived from 14 sheep until day 84, after which each data point represents the mean of 7 sheep necropsied later in the trial. Standard errors have been omitted to aid interpretation. Panel A shows data for IgG, panel B shows data for IgA. "Imm" represents dates on which sheep were immunized; "Trick" represents the trickle infection; "PM" is the post-mortem date.

Figure 10:
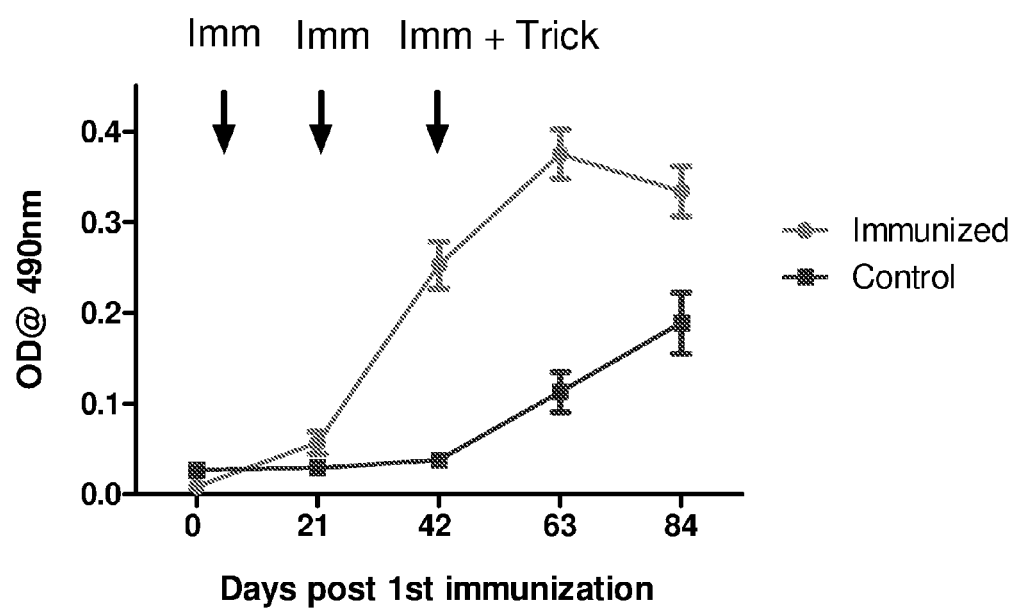

FIG. 10: Serum antibody responses of sheep to L4 excretory/secretory products of *Teladorsagia circumcincta*. 'Imm' represents the days on which animals were immunized with recombinant antigen cocktail (Immunized group) or adjuvant only (Control group).

Figure 11:
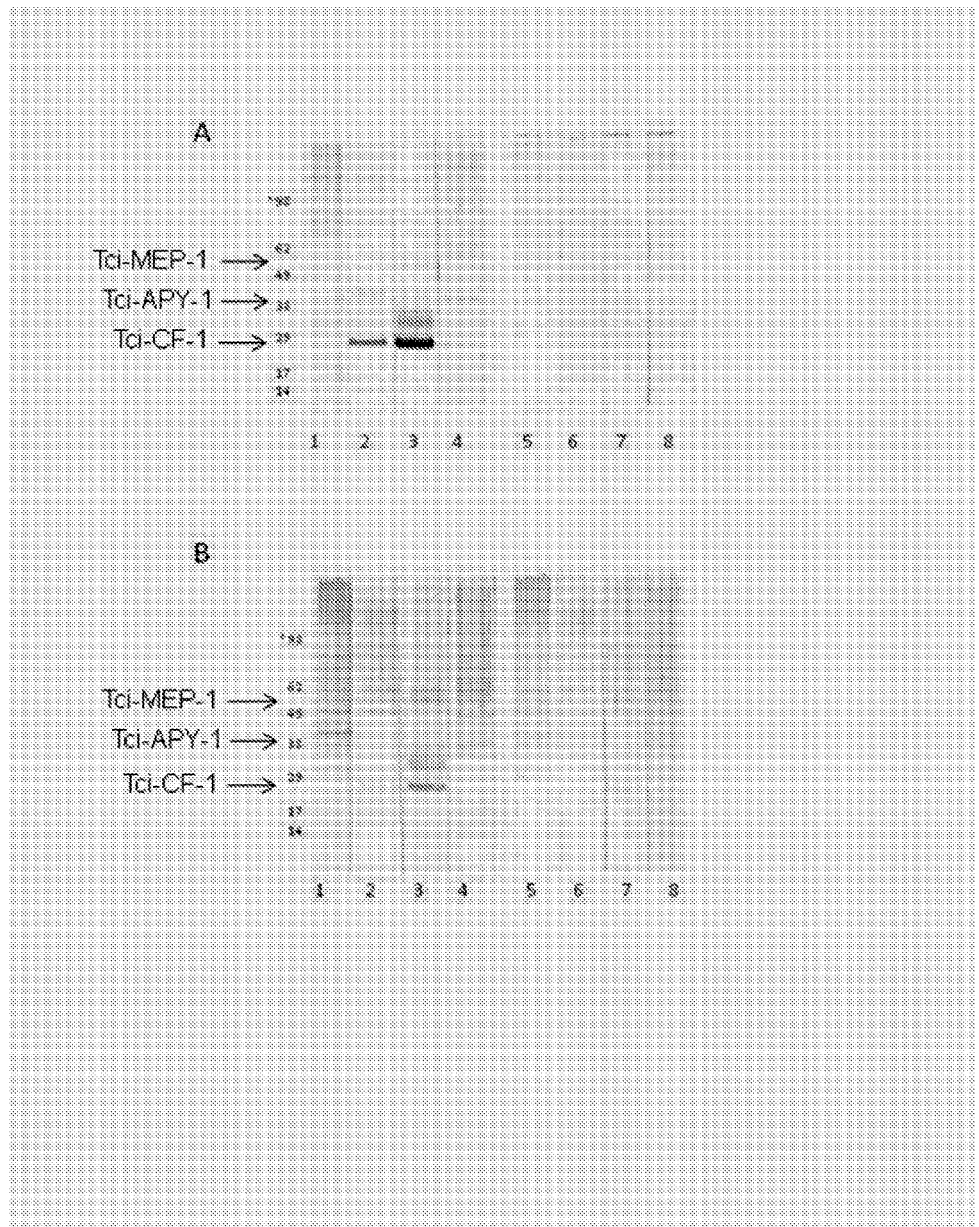

FIG. 11: Immunoblots to investigate serum IgG (Panel A) and IgA (Panel B) binding to components of somatic extracts and excretory/secretory products of *Teladorsagia circumcincta*. Lanes 1 and 5 contain L3 somatic extract, lanes 2 and 6 contain L4 somatic extract, lanes 3 and 7 contain L4 ES material and lanes 4 and 8 contain adult somatic extract. Blots were incubated with sera pooled from 7 immunized sheep (Lanes 1-4, sheep from Group 3, Trial 2) or non-immunized sheep (Lanes 5-8, sheep from Group 4, Trial 2). Sera had been collected from the animals on the date of the third immunization immediately prior to the initiation of trickle infection. * represents molecular mass (kDa).

Figure 12:
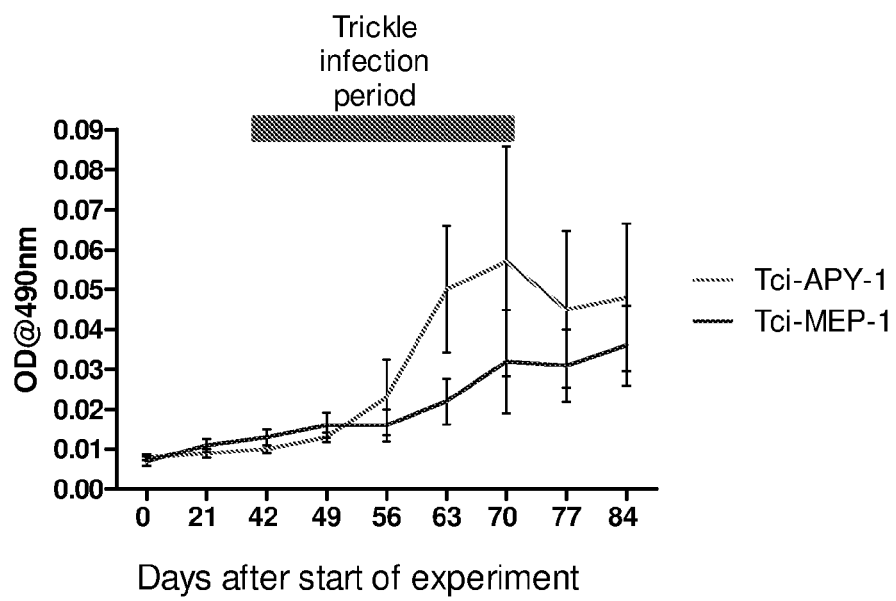
Figure 12:
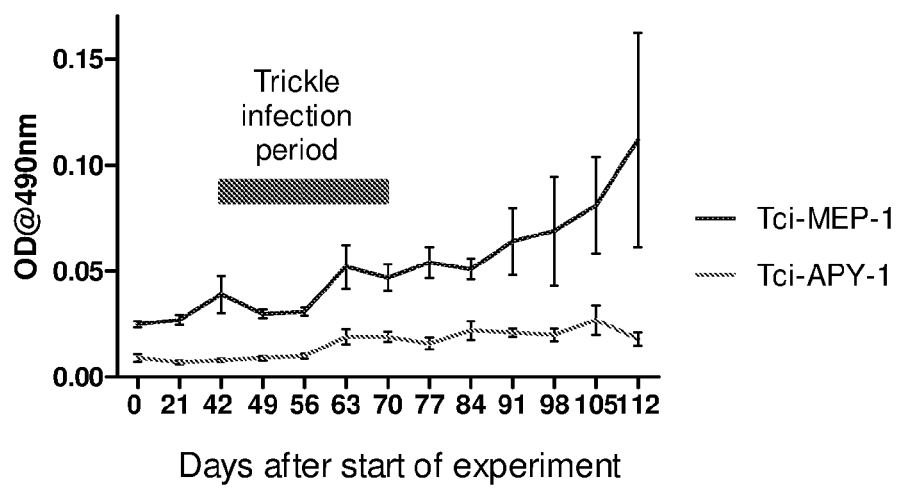

FIG. 12: Serum IgG responses of control, adjuvant only recipients to recombinant Tci-MEP-1 and Tci-APY-1. Each data point represents the mean value (±SEM) derived from 7 (Trial 1, panel A) or 14 (Trial 2, Panel B) sheep until day 84, after which each data point represents the mean of 7 sheep in Trial 2.

Figure 13:
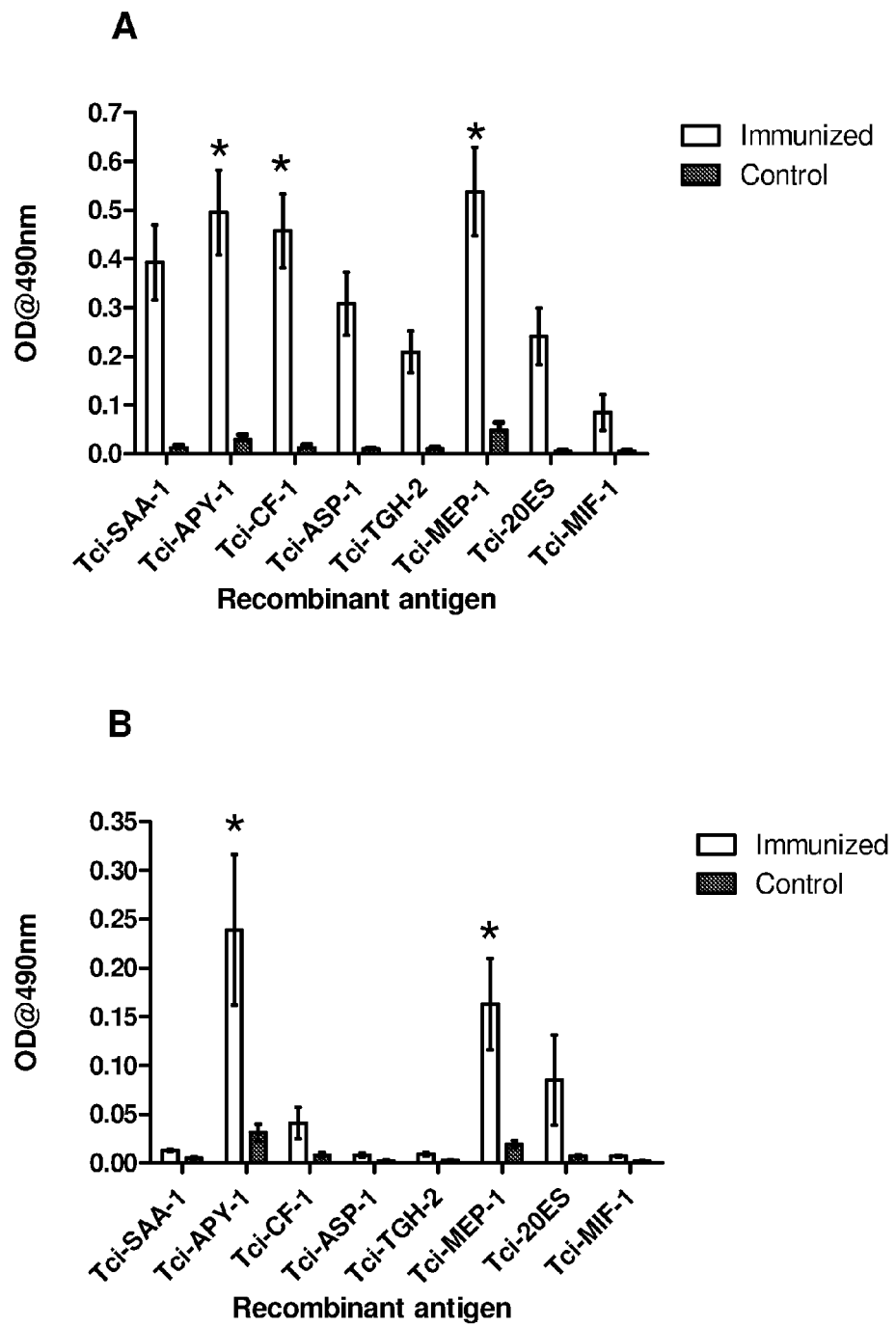

FIG. 13: Mucosal antibody titres to the recombinant proteins used to immunize sheep in Trial 1. Each bar represents the mean value derived from 7 sheep (±SEM). Panel A shows data for IgG, panel B shows data for IgA. Asterisks indicate mean values which are statistically significantly higher than those for the remaining antigens within the same treatment group.

Figure 14:
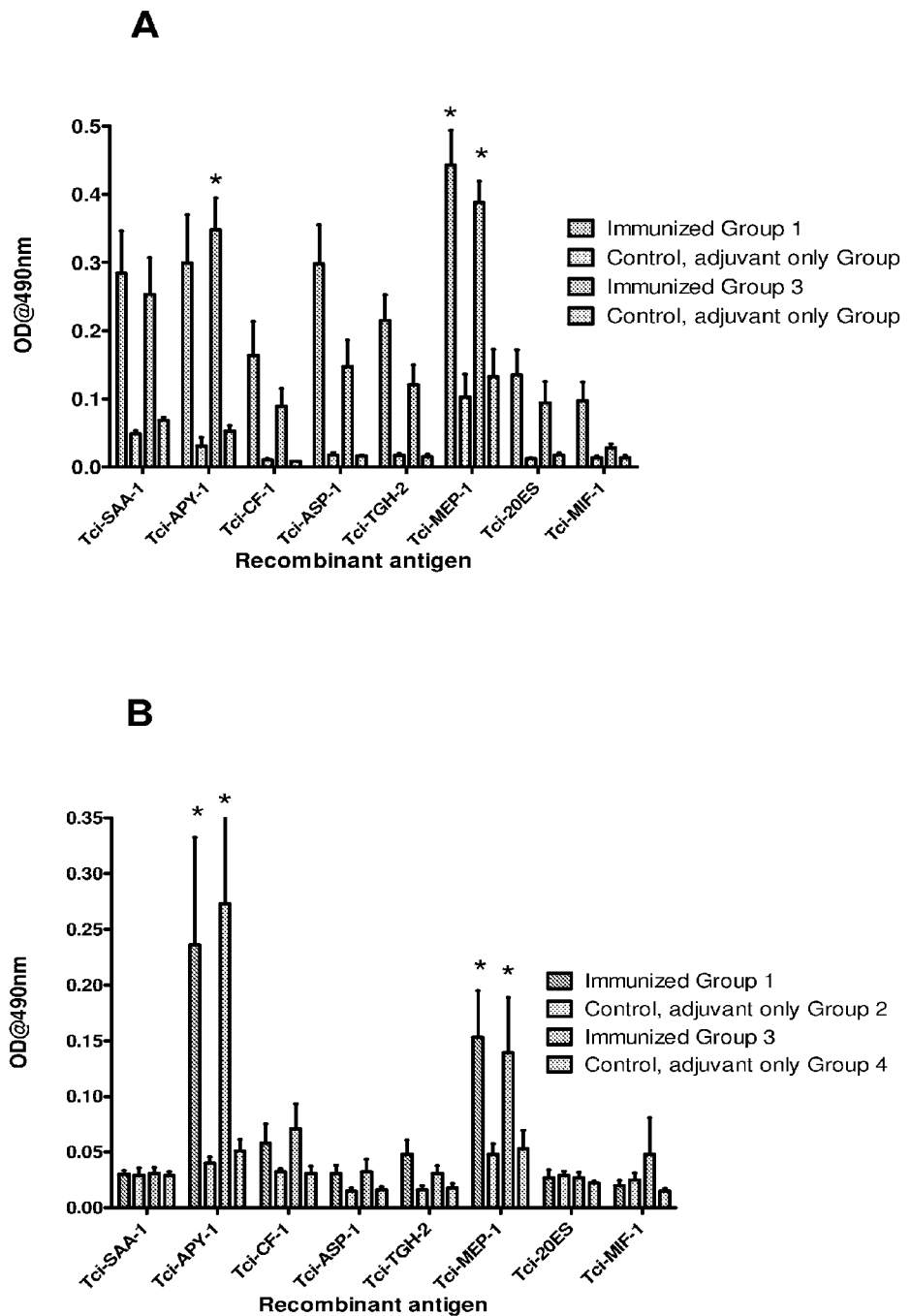

FIG. 14: Mucosal antibody titres to the recombinant proteins used to immunize sheep in Trial 2. Each bar represents the mean value derived from 7 sheep (±SEM). Panel A shows data for IgG, panel B shows data for IgA. Asterisks indicate mean values which are statistically significantly higher than those for the remaining antigens within that Group.

Figure 15A:
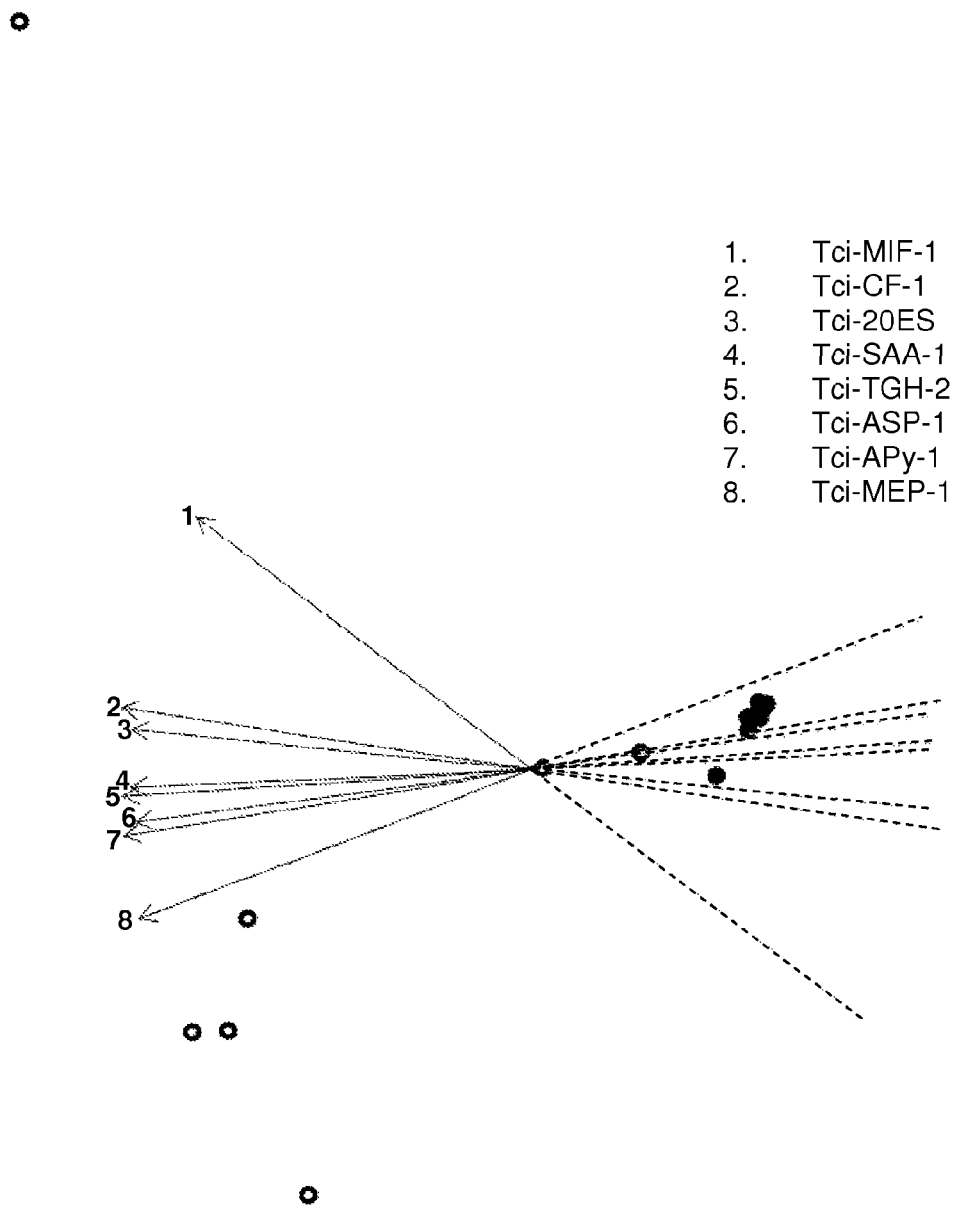
Figure 15B:
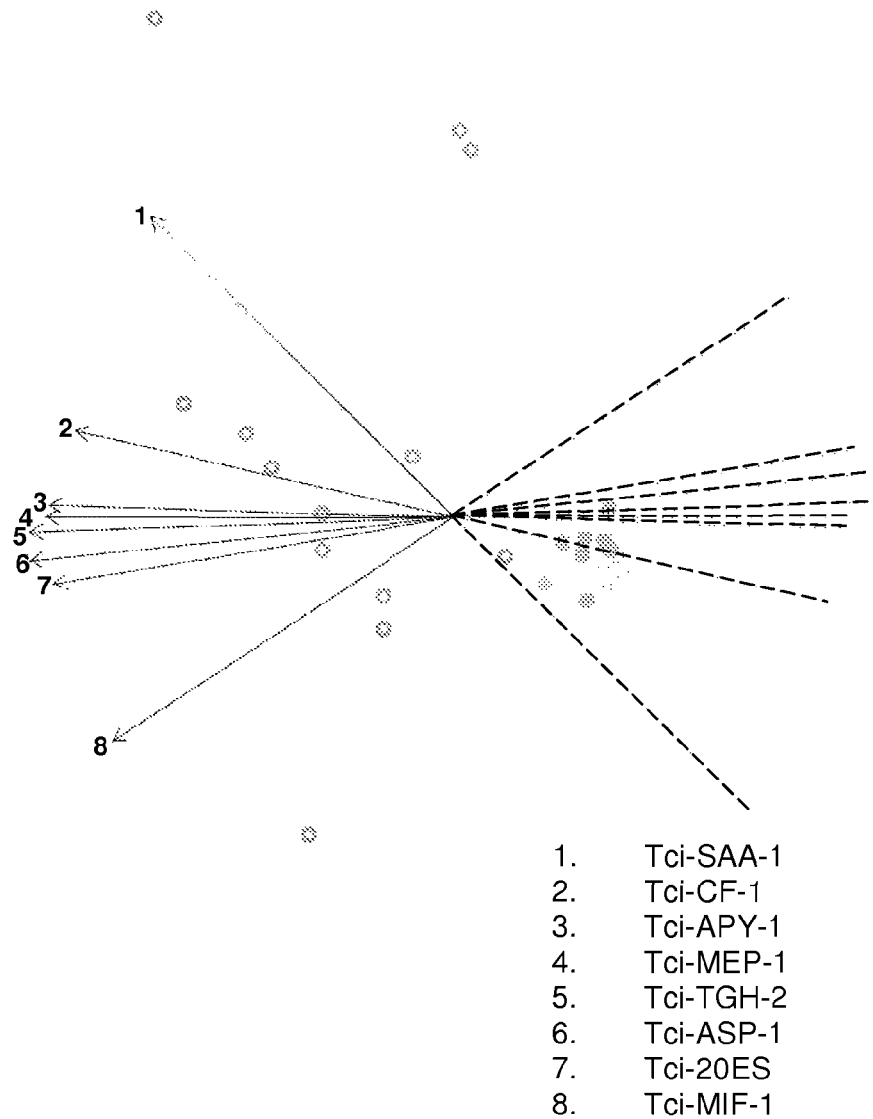
Figure 15C:
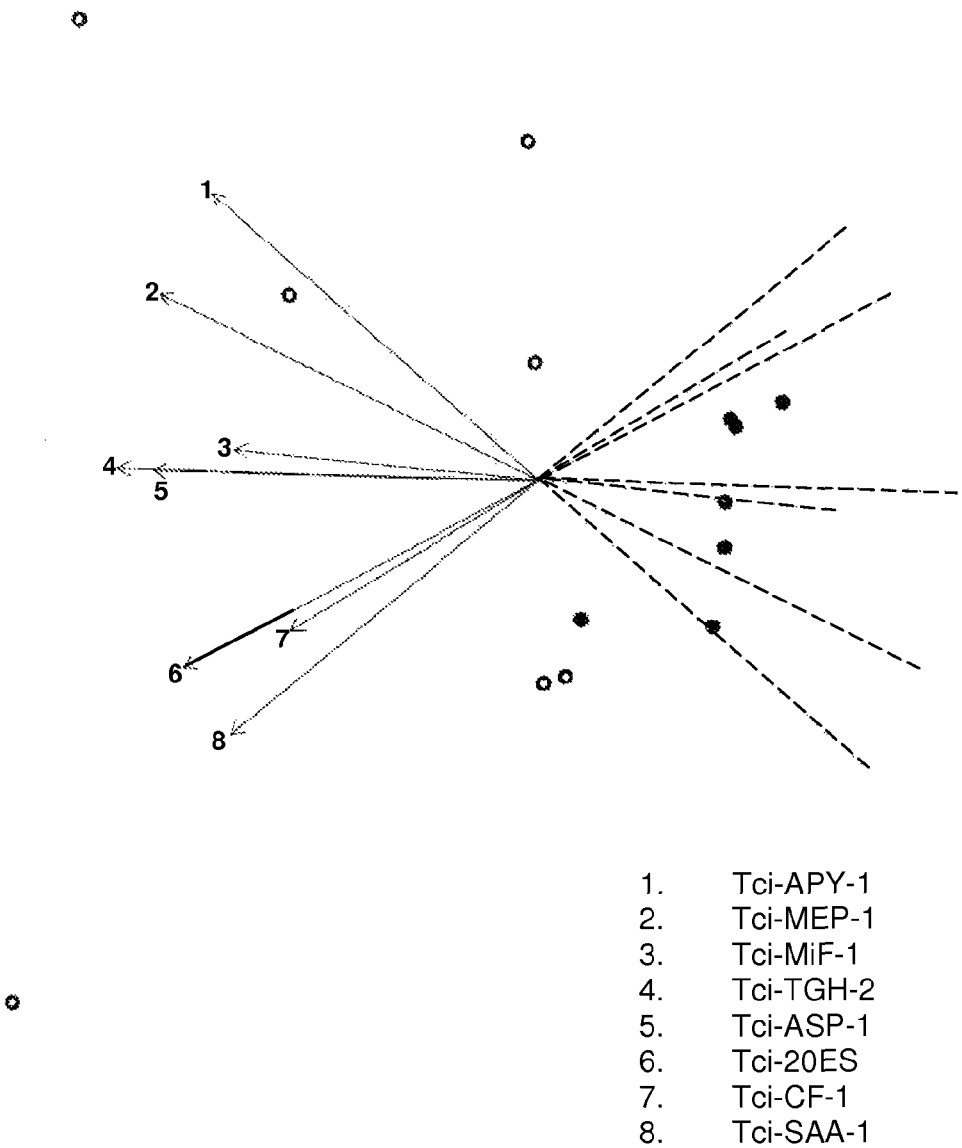
Figure 15D:
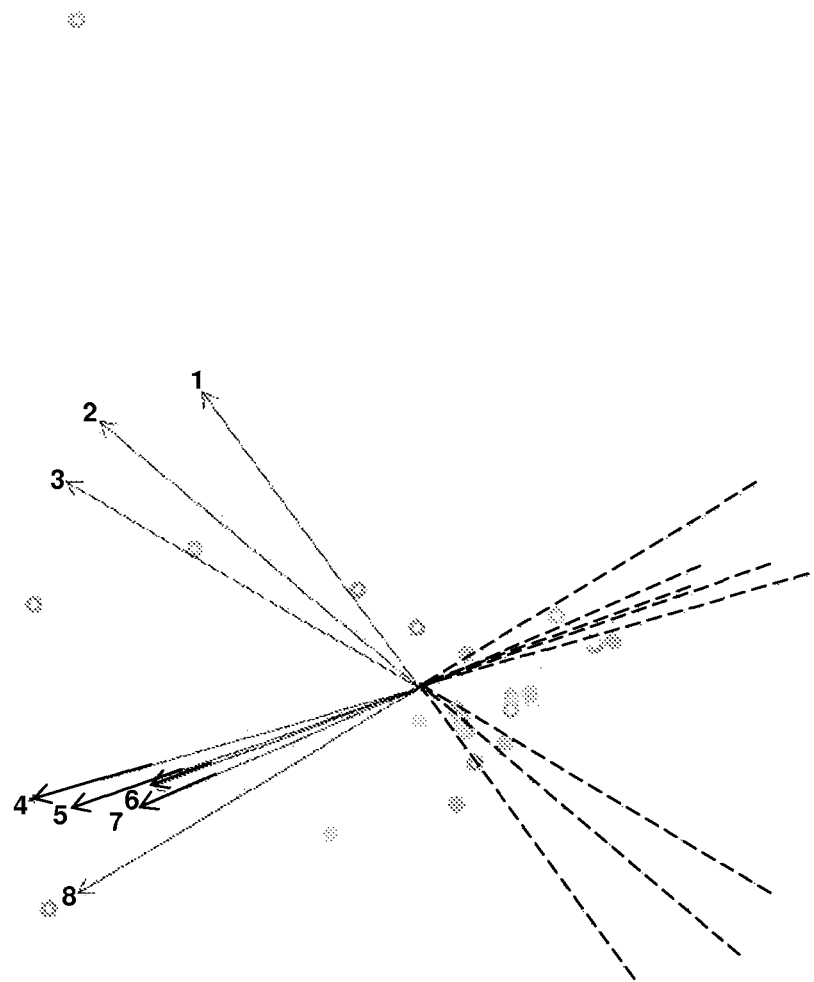

FIGS. 15A-15D: Mucosal antibody levels to the recombinant proteins used to immunize sheep in Trials 1 and 2. FIGS. 15A and 15B show data for IgG, FIGS. 15C and 15D show data for IgA. All graphs show correlation biplots jointly representing sheep (points) and their antigen-specific antibody responses (axes). The arrows indicate directions of higher antigen-specific antibody response. The orthogonal projection of points onto each axis approximates the relative responses by sheep. The correlations between responses to specific antigens are represented by the angle between the corresponding vectors for each antigen. Open circles represent immunized sheep, closed circles represent control, non-immunized sheep. In Trial 2 (FIGS. 15B and 15D), dark grey open circles and light grey open circles represent Groups 1 and 3 (immunized) respectively. Light grey closed and dark grey closed circles represent control Group 2 and 4 respectively.

MATERIALS AND METHODS

Production of Recombinant Proteins for Immunisation

Eight recombinant proteins were used in combination to immunise 6 month-old lambs. Details of these proteins are given in Table 1. Three proteins, macrophage migration inhibitory factor-1 (Tci-MIF-1), calcium-dependent apyrase-1 (Tci-APY-1) and a TGFβ homologue. (Tci-TGH-2) were selected because of their putative immunoregulatory function (McSorley et al., 2009; Nisbet et al., 2010a; Nisbet et al., 2011). The remaining five proteins were selected using a combined immunoscreening/proteomics approach: cathepsin F-1 (Tci-CF-1), astacin-like metalloproteinase-1 (Tci-MEP-1), a 20 kDa protein of unknown function (Tci-ES20) and activation-associated secretory protein-1 (Tci-ASP-1) (Redmond et al., 2006; Smith et al., 2009; Nisbet et al., 2010b). A final protein was chosen because of its homology to known vaccine candidate antigens of other parasitic nematodes. This protein is known as surface-associated antigen (Tci-SAA-1, Nisbet et al., 2009). Cloning and sequencing of the cDNA encoding Tci-SAA-1, Tci-MIF-1 and Tci-APY-1 and production of recombinant versions of each of these proteins in a bacterial expression system have been described previously (Nisbet et al., 2009; Nisbet et al., 2010a; Nisbet et al., 2011). Identical production and purification parameters were employed in the current study. For Tci-MEP-1, oligonucleotide primers for use in the rapid amplification of cDNA ends (RACE) were designed from the EST sequence CB036707 and RACE performed using the SMART™ RACE kit (Clontech) according to the manufacturer's instructions, using total RNA extracted from L4 stage *T. circumcincta* (prepared as described in Nisbet et al., 2008) as a template. Amplification of the full coding sequence (CDS) of Tci-mep-1 was performed using oligonucleotide primers incorporating the initiation and termination codons from the contigs generated by 5' and 3' RACE, cDNA generated from L4 as template (prepared as described in Redmond et al., 2006) and the ADVANTAGE® 2 PCR Kit (Clontech) according to the manufacturer's instructions. Following confirmatory sequencing, oligonucleotide primers were designed to amplify the CDS of Tci-mep-1, omitting the sequence encoding the signal peptide (bases 1-48 of the CDS) and the termination codon. Using these primers, plasmid containing the full-length CDS as a template and the ADVANTAGE® 2 PCR Kit (Clontech), Tci-mep-1 was amplified and sub-cloned into the expression vector pET SUMO (Invitrogen). The resulting plasmid was used to transform *Escherichia coli* BL21-CodonPlus® (DE3)-RIL competent cells (Stratagene). Recombinant protein expression was induced in the presence of 1 mM isopropyl β-D-1-thiogalactopyranoside (IPTG). Insoluble recombinant Tci-MEP-1 was purified from inclusion bodies solubilised in 8M urea, followed by nickel column affinity chromatography using HisTrap™ HP columns (GE Healthcare) and a step-wise imidazole gradient in the presence of 8M urea in 20 mM phosphate buffer, pH 7.6. Purified Tci-MEP-1 was then dialysed against 2M urea in 20 mM phosphate buffer, pH 7.6. The full CDS of the cDNA encoding Tci-TGH-2 (accession number FJ410914) was amplified by PCR using oligonucleotide primers incorporating the initiation codon, but omitting the termination codon. Plasmid containing the full CDS in a cloning vector was used as a template (kindly supplied by Prof Rick Maizels, University of Edinburgh) and the Advantage® 2 PCR Kit (Clontech) was employed according to the manufacturer's instructions. Tci-tgh-2 was sub-cloned into the expression vector pET SUMO (Invitrogen) and recombinant protein expression performed as described above. Soluble recombinant Tci-TGH-2 was purified from cell lysates by nickel column affinity chromatography using HisTrap™ HP columns (GE Healthcare). Next, rTci-TGH-2 was eluted in 500 mM imidazole, 20 mM phosphate buffer, pH 7.6 and then dialysed against 20 mM phosphate buffer, pH 7.6 at RT for 3 hrs. Sub-cloning of the CDS of Tci-asp-1 (after removal of the bases encoding the signal peptide) from a pET22b(+) vector (described in Nisbet et al., 2010b) into pET SUMO, using the conditions outlined above for Tci-tgh-2, permitted the expression of soluble recombinant Tci-ASP-1 which was expressed and then purified by nickel column affinity chromatography as described, above, for Tci-TGH-2. For the expression of Tci-CF-1 protein, oligonucleotide primers were designed to amplify the CDS of Tci-cf-1, omitting the sequence encoding the signal peptide (bases 1-42 of the CDS) and the termination codon. Using these primers, cDNA generated from L4 as template (prepared as described in Redmond et al., 2006) and the Advantage® 2 PCR Kit (Clontech), Tci-cf-1 was sub-cloned into the vector pPICZαC (Invitrogen) and used to transform the yeast *Pichia pastoris* [X-33 Mut$^+$ strain (Invitrogen)]following linearisation with PmeI (New England Biolabs). Recombinant protein expression was induced in the presence of 0.5% methanol, as described in Nisbet et al. (2007) and soluble recombinant Tci-CF-1 was purified from culture supernatant by nickel column affinity chromatography as described above for Tci-TGH-2. Tci-ES20, a homologue of a 20 kDa excretory/secretory (ES) protein of *Ostertagia ostertagi*, was identified during an immunoscreening/proteomic analysis of immunogenic *T. circumcincta* ES molecules (Smith et al., 2009). The complete coding sequence was determined by obtaining the putative full-length cDNA via polymerase chain reaction (PCR) amplification from a cDNA library. This SMART™ cDNA library was constructed [using *T. circumcincta* L4 (8 days post infection, dpi) RNA) in λTriplEx2 by long-distance PCR following manufacturer's instructions (Clontech). It was packaged using Gigapack Gold III packaging extract (Stratagene) and amplified in *E. coli* XL1-Blue cells (Stratagene). A gene-specific oligonucleotide primer (incorporating the putative termination codon identified from EST CB043664) was used in conjunction with a vector-specific primer to amplify the Tci-es20 CDS directly from a heat-denatured phage lysate preparation of the library. The resultant amplicon was column-purified (QIAquick PCR purification kit, Qiagen) and ligated into pGEM®-T (Promega). Constructs were transformed into *E. coli* JM109 (Promega), colonies with Tci-es20-containing plasmids were isolated and propagated and the plasmids subjected to automated sequencing (Eurofins MWG operon). The cDNA encoding Tci-ES20 was then subcloned into the vector pPICZαC (Invitrogen) and used to transform *P. pastoris* [X-33 (Mut$^+$) strain (Invitrogen)] following linearisation with PmeI (New England Biolabs). Recombinant protein expression and purification were as described, above, for Tci-CF-1. Protein concentrations were determined using the Pierce BCA™ (bicinchoninic acid) assay (Thermo Scientific) with bovine serum albumin (BSA) standards and stability and integrity of each recombinant protein were monitored using SDS-PAGE. Tci-MIF-1; Tci-APY-1; Tci-SAA-1; Tci-CF-1; Tci-ES20 and Tci-MEP-1 were stored in solution at +4° C. and Tci-ASP-1 and Tci-TGH-2 were stored at −20° C.

challenge was initiated whereby each sheep in both groups was administered with 2000 *T. circumcincta* L3. This was continued three times per week (Monday, Wednesday and Friday) for 4 weeks. Blood samples were taken prior to each immunisation and weekly samples taken from the day of the third immunisation onwards to determine antigen-specific serum IgA and IgG responses and serum pepsinogen levels (Lawton et al., 1996). FECs were performed (Christie and Jackson 1982) three times per week (Monday, Wednesday and Friday) from 14 days after the start of the trickle

TABLE 1

Recombinant proteins used in *Teladorsagia circumcincta* vaccine trial

| Name | Accession number | Function* | Expression system | Reference |
|---|---|---|---|---|
| Tci-SAA-1 | CAQ43040 | L3-enriched surface associated antigen | pET22b(+) *E. coli* BL21 (DE3)-RIL | Nisbet et al., 2009 |
| Tci-MIF-1 | CBI68362 | L3-enriched macrophage migration inhibitory factor | pET22b(+) *E. coli* BL21 (DE3)-RIL | Nisbet et al., 2010a |
| Tci-ASP-1 | CBJ15404 | L4-enriched activation-associated secretory protein | pET SUMO *E. coli* BL21 (DE3)-RIL | Nisbet et al., 2010b |
| Tci-TGH-2 | ACR27078 | Transforming growth protein 2-like protein | pET SUMO *E. coli* BL21 (DE3)-RIL | McSorley et al., 2010 |
| Tci-CF-1 | ABA01328** | L4-enriched Secreted cathepsin F | pPICZαC *Pichia pastoris* X33 strain | Redmond et al., 2006 |
| Tci-ES20 | Not yet submitted*** | Excretory/secretory (ES) protein | pPICZαC *Pichia pastoris* X33 strain | Smith et al., 2009 |
| Tci-MEP-1 | Not yet submitted*** | Astacin-like ES metalloproteinase | pET SUMO *E. coli* BL21 (DE3)-RIL | Smith et al., 2009 |
| Tci-APY-1 | CBW38507 | L4-enriched ES calcium-activated apyrase | pSUMO *E. coli* BL21 (DE3)-RIL | Nisbet et al., 2011 |

*Putative or inferred function
**Tci-CF-1 is highly polymorphic, the clone used for vaccine production had following amino acid substitutions compared to published sequence. In each case the amino acid in the published sequence is in italics, that in the vaccine isoform sequence is in normal font and the amino acid position in the published sequence is in subscript:
$I_{44} \Rightarrow T_{44}$, $N_{101} \Rightarrow D_{101}$, $T_{129} \Rightarrow A_{129}$, $R_{137} \Rightarrow Q_{137}$, $R_{305} \Rightarrow K_{305}$, $L_{306} \Rightarrow P_{306}$, $S_{307} \Rightarrow Y_{307}$
***Full length sequences not yet deposited. These molecules have been derived from EST data in the public domain: Tci-ES20 based on CB043664, Tci-MEP-1 based on CB036707

Immunisation Trial

Fourteen, Texel crossbred male/female sheep which had been raised in conditions to minimise helminth infection risk, were housed in two groups of 7 animals in separate pens within the same building. The sheep were 204-206 days old at the initiation of the experiment. Faecal egg counts (FEC, Christie and Jackson 1982), performed prior to initiation of the experiment, confirmed that all animals had negative FECs. Sheep in Group 1 were immunised by subcutaneous injection using a 400 μg recombinant protein mix (incorporating 50 μg each Tci-ASP-1; Tci-MIF-1; Tci-TGH-2; Tci-APY-1; Tci-SAA-1; Tci-CF-1; Tci-ES20; Tci-MEP-1 in PBS) plus 5 mg total Quil A (Brenntag Biosector). Seven of the 8 recombinant proteins were PBS-soluble and were administered as a mixture in a single injection with 2.5 mg Quil A. Tci-MEP-1 was insoluble in PBS and was therefore formulated with 100 mM urea in PBS plus 2.5 mg Quil A. The two preparations were injected subcutaneously, one immediately following the other, at two sites on the neck of each sheep. Each sheep received three immunisations of the recombinant protein mix with an interval of 3 weeks between each immunisation. Sheep in the control group (Group 2) each received three immunisations with urea/PBS/Quil A only, at the same time as the sheep in Group 1. On the day of the third immunisation, an oral trickle challenge, until the end of the experiment 5 weeks later. All sheep were weighed weekly. For both groups, abomasal swab samples were collected at post-mortem (Smith et al., 2009) to determine levels of antigen-specific IgA and IgG antibody at the abomasal mucosal surface. At necropsy, lumenal and mucosal nematode burdens (adult and larval parasites) were enumerated following standard techniques. The percentage of stunted or "inhibited" larvae was determined, based on size, as described previously (Halliday et al., 2010). The experiment was performed under the regulations of a UK Home Office Project Licence.

Trial 2

Twenty-eight, Texel crossbred male/female sheep were raised as described for Trial 1 and were housed in four groups of 7 animals. The sheep were 172-178 days old and were not excreting helminth eggs at the start of the experiment. Groups 1 and 3 were immunized by subcutaneous injection using the recombinant protein mix exactly as described for Trial 1, with each sheep receiving three immunizations with an interval of 3 weeks between each. Sheep in Groups 2 and 4 each received three immunizations with urea/PBS/Quil A, at the same time as Groups 1 and 3. At the final immunization, the oral trickle challenge commenced in all Groups and all biological samples were obtained as described above, for Trial 1. Sheep in Groups 1 and 2 were euthanized 7 weeks after the start of the infection period (as for Trial 1) and those in Groups 3 and 4 were euthanized 4 weeks later. For all groups, lumenal and mucosal nematode burdens were enumerated as described for Trial 1. Trial 1 and Trial 2 were performed under the strict regulations of a UK Home Office Project Licence and the experimental design was ratified by the Moredun Research Institute Experiments and Ethics Committee.

Measurement of Antibody Responses to Recombinant Antigens

Following initial antibody:antigen titrations to ensure optimisation of the technique, antigen-specific antibody levels in serum and abomasal mucus samples were assessed by ELISA. High binding microtitre plates (Greiner Bio-One) were coated overnight at 4° C. with 50 μl antigen (5 μg ml$^{-1}$ in 50 mM carbonate buffer, pH 9.6). Plates were washed six times with wash buffer [phosphate buffered saline (PBS), 0.05% v/v Tween-20], then blocked with 5% soya milk powder in 0.5% (v/v) Tween 20 in Tris Buffered Saline (TTBS), pH 7.4, for 1 h at room temperature. After washing, 50 μl abomasal mucus (diluted 1:4 in TTBS) from individual animals or 50 μl serum [diluted at 1:10 (IgA) or 1:1000 (IgG) in TTBS], were added and incubated for 1 h at room temperature. Wells were re-washed and 50 μl horseradish peroxidase-conjugated polyclonal mouse anti sheep/goat IgG (A9452, Sigma) at 1:1000 or 50 μl mouse anti-bovine/ovine IgA monoclonal antibody (Serotec, MCA628) at 1:250 in TTBS, were added for 1 h at room temperature. After a further wash, the IgG ELISA was developed by the addition of 50 μl o-phenylenediamine dihydrochloride substrate (OPD, Sigma) to each well. After 15 min in darkness, the reaction was stopped by addition of 25 μl 2.5M $H_2SO_4$ and OD values read at 490 nm. For the IgA ELISA, 50 μl horseradish peroxidase-conjugated polyclonal rabbit anti-mouse IgG (P0260, DakoCytomation), at 1:1,000 were added for 1 h at room temperature prior to a final wash and development with OPD as described above. Each sample was assayed in triplicate. OD values were corrected against a reagent blank and all test plates had a positive and negative serum control to account for plate to plate variation.

Measurement of Antibody Responses to Native *T. circumcincta* Antigens

Antigen-specific IgG levels in the sera of sheep which had been immunized with the recombinant antigen cocktail, or the non-immunized control sheep, were assessed by ELISA. The native antigens used to coat ELISA plates were somatic extracts of *T. circumcincta* L3, prepared as described previously (Nisbet et al., 2009), along with L4 ES products, prepared as described in Smith et al., (2009). Antigen-specific IgG levels were assessed in all sera from animals in Trial 1 and from four, randomly selected, animals from Groups 1 and 2 of Trial 2. All experimental conditions were as described, above, for the determination of recombinant antigen-specific IgG levels in serum by ELISA.

Immunoblotting of Nematode Somatic Extracts

Somatic extracts of *T. circumcincta* L3, L4 and adult worms, prepared as described previously (Nisbet et al., 2009), along with L4 ES products, prepared as described in Smith et al., (2009), were subjected to immunoblotting using serum, collected on the date of the third (final) immunization immediately prior to the initiation of trickle infection, from immunized or non-immunized sheep. Immunoblotting, to determine serum IgG and IgA binding to components of each extract, was performed as described previously (Nisbet et al., 2009) using pools of serum from 7 immunized (Group 3) and 7 non-immunized sheep (Group 4).

Statistical Analysis

A generalised additive mixed modelling (GAMM) approach was adopted for the analysis of longitudinal FEC data. A GAMM model on log(FEC+1) was specified with Gaussian error structure and identity link function, with group as a fixed effect and animal effects introduced as random. The model included separate smoothing curves to model the nonlinear relationship of the response with time by group and non-homogenous within-group variances were allowed. A first order autoregressive residual correlation structure was incorporated. Serum and mucosal antibody responses to individual antigens were modelled using linear mixed models (LMMs) with group as a fixed effect and animal as a random effect. For serum antibody data, repeated measures over time were modelled by random intercept and slope LMMs also including time and its interaction with group as a fixed effect. Heterogeneous within-group variances were allowed in all cases. Linear contrasts were set up to compare subsets of antigen-specific responses in abomasal mucus at post mortem.

In Trial 2, the 28 animals were housed in 4 separate groups (pens) of 7 animals for logistical reasons. Two groups (14 animals) were immunized (Group 1 and Group 3), and the other two (14 animals) were used as adjuvant-only controls (Group 2 and Group 4). Pen effects between the two immunized groups (1 and 3) and between the two adjuvant-only groups (2 and 4) were tested. No statistically significant pen effects were found for any of the above response types, so Groups 1 and 3 were combined and Groups 2 and 4 were combined for data modelling. For analysis of worm burden data, generalised linear models (GLMs) were used. Data overdispersion was detected and it was generally accounted for by specifying a negative binomial error distribution. Where necessary, overdispersion was incorporated using Poisson GLMs correcting the standard errors by specifying the mean and variance relationship. Nematode burdens were assessed at post mortem in Groups 1 and 2 four weeks before those of Groups 3 and 4, so data were analysed separately.

Model selection was based on the Akaike's information criterion (AIC) and likelihood ratio tests (LRT) (Akaike, 1974). The mixed models were fitted by residual maximum likelihood (REML; Smouse and Kojina, 1972). Throughout the data analysis some animal measurements were identified as outliers. Their influence on parameter estimates was considered in each case. The Cook's distance with a 4/n cut-off value was used to support decisions in relation to outlying values (Cook, 1977). Statistically significant terms were determined at the level of 0.05. All statistical analyses were conducted using R version 2.13.

Results

FECs Analysis

Trial 1: FEC data is shown in FIGS. 1A and B. Sheep in both immunised and control groups began to excrete trichostrongyle type eggs in their faeces from 16-19 days after the start of the trickle challenge. In both groups, FECs rose until 23 days after the start of challenge. Thereafter, sheep in Group 1 excreted substantially fewer eggs than those in Group 2. By the end of the experiment, at day 42 of the trickle challenge, Group 1 sheep were producing a mean of 8.7 (±5.5) eggs per gramme (EPG) of faeces, whereas sheep in Group 2 were producing 107.6 (±50.8) EPG, representing a reduction of 92% in mean FEC at that time-point. REML (GAMM) analysis identified an overall effect of treatment (immunization) (P=0.003) and time (P<0.001), and a significant treatment×time interaction (P=0.20). The mean cumulative FECs for the duration of the experiment, estimated by taking the sum of all egg counts on each sampling date, were 252 (±132) EPG in Group 1 and 890 (±231) EPG in Group 2, representing an overall mean FEC reduction of 72% in the immunised versus the control group. FEC Mean cumulative FECs for the duration of the challenge period, calculated using the area under the curve (AUC, Taylor et al., 1997) technique were 595 (±316) EPG in Group 1 and 1975 (±532) EPG in Group 2, representing an overall reduction of 70% in the immunized versus the control (adjuvant only) group (FIG. 1B).

In Trial 2, sheep began to excrete nematode eggs from 14-16 days after challenge (FIG. 1C). At peak egg shedding, on day 86, mean FECs in the extant immunized group (Group 3) were 251±75 EPG, whereas in the control group (Group 4) they were 908±158 EPG, representing a 73% reduction in mean FEC. Mean cumulative FECs, calculated using the area under the curve (AUC, Taylor et al., 1997) technique, in Trial 2 were 4998 (±) 2233 EPG in Group 1 (immunized) and 4127 (±) 803 EPG in Group 2 (adjuvant only, FIG. 1D). The high mean FECs, and associated SEM, in Group 1 were attributable to the influence of data from a single outlier animal (sheep 675J, FIG. 1D). Influence was assessed using Cook's distance criterion (Cook, 1977): 675J was regarded as a "highly influential" case (Cook's distance=0.3129 based on a LMM model). For Groups 3 and 4, which were necropsied 4 weeks after Groups 1 and 2, mean cumulative FECs were 7005 (±) 681 EPG in Group 3 (immunized) and 16727 (±) 2,699 EPG in Group 4 (control, adjuvant only), representing an overall mean FEC reduction of 58% in the immunized versus the control group (FIG. 1D). GAMM analysis indicated a statistically-significant effect of immunization (data from Groups 1 and 3 combined vs. Groups 2 and 4 combined as detailed in Materials and Methods) on FEC over the course of the experiment (P=0.0237).

Abomasal Parasite Burdens

Trial 1: Preliminary Analysis

Abomasal *T. circumcincta* enumerations were subdivided into lumenal and mucosal burdens. Within the lumen, Group 1 sheep had significantly fewer adult male (P=0.004) and female *T. circumcincta* (P=0.011, FIG. 2, Panel A) than was observed in the Group 2 sheep. There was no significant difference in parasite gender ratio between the two groups. Taking all developmental stages and genders into account (FIG. 2, Panel B) Group 1 harboured significantly fewer luminal parasites than the sheep in Group 2 (P=0.0037)-sheep in Group 1 had 72% less nematodes in the abomasal lumen than those in Group 2. Within the mucosa, the numbers of adult female worms in Group 1 were significantly less than those observed in Group 2 (P=0.016) (FIG. 3). There was no significant difference between the numbers of male worms or larval stages enumerated in the mucosa in the two groups, although fewer male worms were enumerated in Group 1 sheep and fewer larval stages in Group 2 sheep (FIG. 3).

Trial 1: Supplementary Analysis of Total Worms Numbers (Lumenal Plus Mucosal)

Immunized sheep (Group 1) harboured 55% fewer *T. circumcincta* (total of adults and larvae) at necropsy than control, adjuvant only (Group 2) sheep (P=0.011, FIG. 4, Panel A). Group 1 sheep had statistically-significantly lower mean adult nematode burdens than sheep in Group 2 (75% reduction, P=0.0066, FIG. 4, Panel B). Comparison of juvenile nematode burdens in the abomasum indicated no significant differences between the two groups (FIG. 4, Panel C). No significant differences were observed in the length of worms recovered from the different groups (data not shown).

Liveweight Gain

The average increase in weight from Day 0-Day 84 of sheep in Group 1 was 2.1 kg more than that observed in sheep in Group 2 (p=0.10) (FIG. 5).

Trial 2

Groups 1 and 2 (Post Mortem at Day 84):

The total abomasal nematode burdens (adults and larvae) in immunized sheep were not statistically significantly different to the control, adjuvant only group (mean total nematode burdens: Group 1; 6843±1144, Group 2; 6250±966). When adult nematode burdens and juvenile nematode burdens were analysed separately, the adult nematode burdens in immunized sheep were not statistically significantly different to the control, adjuvant only group. Comparison of the juvenile nematode burdens indicated that immunized sheep had fewer juvenile nematodes than control, adjuvant only sheep in the abomasal lumen (Group 1: 50±42; Group 2: 218±81), (FIG. 6). Because of the preponderance of "zero" values in the counts from the immunized sheep, statistical analysis using models was unreliable in this case. Conversely, there were more juvenile stages in the abomasal mucosa of Group 1 than Group 2 (Group 1: 643±198; Group 2: 114±70; P=0.0367, FIG. 6).

Groups 3 and 4 (Post Mortem at Day 112):

Immunised sheep (Group 3) harboured 57% fewer *T. circumcincta* total nematodes at necropsy than did the control, adjuvant only (Group 4) recipients (P=0.0199, FIG. 7). In both Groups 3 and 4, adult worms comprised 99% of the total nematode burden and no significant difference in the numbers of juvenile stages was observed between the two Groups.

Measurement of Serum Antibody Responses to *T. circumcincta* Antigens

In both trials, following tertiary immunization, serum IgG levels against all recombinant proteins reached peak levels, which declined slowly thereafter (FIGS. 8, Panel A and 9, Panel A). Serum IgA levels peaked after secondary immunization and, for all recombinants, with the exception of Tci-MIF-1, levels remained relatively constant until the end of the experiment (FIGS. 8, Panel B and 9, Panel B). Following immunization with the recombinant antigens, sheep produced serum IgG, prior to parasite challenge, which bound native L4 ES components (FIG. 10). The nature of the immunoreactive antigens in this ES material, and other *T. circumcincta* extracts, was investigated further by immunoblotting: IgG bound to parasite components, in somatic extracts of L4 and adult *T. circumcincta* as well as L4 ES, of the expected size range for the following vaccine components, Tci-CF-1 (23.9 kDa), Tci-APY-1 (38.6 kDa) and Tci-MEP-1 (55.6 kDa) (FIG. 11, Panel A). IgA also bound parasite components, in somatic extracts of L4 and adult *T. circumcincta* and L4 ES, of the expected size range for the vaccine components, Tci-CF-1, Tci-APY-1 (Adult only) and Tci-MEP-1 (FIG. 11, Panel B). In addition IgA bound an unknown parasite component of ca. 43 kDa in L3 somatic extract.

In both Trials 1 and 2, from 14 days after initiation of challenge, control, adjuvant only recipients generated serum IgG that bound recombinant Tci-MEP-1 and Tci-APY-1 (FIG. 12). Antigen-specific serum IgA which bound to the recombinant proteins was not observed in the control, adjuvant only recipients (data not shown).

Measurement of Antibody Responses to Recombinant Antigens in Abomasal Mucus

In Trial 1 and 2, mean recombinant antigen-specific mucosal IgG levels in abomasal mucus of the immunized sheep were significantly higher than in the control, adjuvant only recipients for each protein (FIGS. 13, Panel A and 14, Panel A). In Trial 1, mean Tci-APY-1-, Tci-MEP-1-, and Tci-CF-1-specific IgG levels were significantly higher than those measured against the other five recombinants (P<0.0001), whereas in Trial 2, mean Tci-MEP-1-specific IgG levels were significantly higher than responses to the remaining antigens (Day 84 necropsy) while Tci-MEP-1- and Tci-APY-1-specific IgG levels were significantly higher at the Day 112 necropsy. A joint biplot representation of animals and antigen-specific mucosal IgG responses (FIGS. 15A and 15B) illustrates the relationships between treatments, between animals within groups, with respect to IgG responses to the different antigens and overall differences between immunized and control, adjuvant only sheep.

Mucosal Tci-APY-1- and Tci-MEP-1-specific IgA levels were significantly higher than those directed against the other six recombinant antigens in Trial 1 and 2 (FIGS. 13, Panel B and 14, Panel B). The overall differences between immunized sheep and adjuvant only recipients are represented in joint biplots of animals and antigen-specific mucosal IgA responses in FIGS. 15C and 15D.

DISCUSSION

Here, we demonstrated that immunisation of sheep with a cocktail of eight recombinant *T. circumcincta* proteins results in significant levels of protection in terms of FECs and parasite burdens when compared to challenge control sheep. As far as we are aware, this is the first published report of successful vaccination against this nematode species using a recombinant vaccine. Indeed, the levels of protection are higher than observed in any other system using a recombinant vaccine against a parasitic nematode in the definitive ruminant host. The level of protection achieved, in terms of FEC and abomasal luminal burden, is similar to the highest reported levels following vaccination with detergent extracts of *T. circumcincta* L3 (Wedrychowicz et al., 1992; 1995). In those experiments immune anti-parasite responses were variable, but parasite burdens were significantly reduced (by up to 72%) and FECs were reduced by more than 70%. The antigens that stimulated protection in the previous trials (Wedrychowicz et al., 1992; 1995) were not characterised in detail and their identity remains elusive.

Other attempts to protect sheep against *T. circumcincta* using native antigen preparations, for example lectin-binding integral membrane glycoproteins, have not been successful (Smith et al., 2001). This general lack of success in immunisation against *T. circumcincta* is in contrast to the situation in other, closely related, parasitic nematode species. For example, the closest homologues of Tci-ASP-1, the N-type single domain ASPs, Oo-ASP-1 and Oo-ASP-2, are the principal components of an ASP-enriched native extract of adult *Ostertagia ostertagi* which has been used with success in vaccination trials in cattle (Geldhof et al., 2002, 2004; Meyvis et al., 2007). However, vaccination with a recombinant version of Oo-ASP-1 has failed to induce either protective immunity or native-antigen specific antibodies in vaccinated calves (Geldhof et al., 2008). This reflects the outcomes of many nematode vaccine trials using recombinant versions of native proteins/complexes where the native molecules show great promise, but where recombinant versions fail to induce protective immunity (Geldhof et al., 2007). This "pragmatic" approach to antigen identification, where protective native extracts are identified by an iterative process of fractionation and vaccination and recombinant versions of single (or multiple e.g. see Cachat et al., 2010) protective antigens are produced and tested in vivo, therefore appeared to be of limited value for the development of a vaccine against *T. circumcincta*.

The approach to antigen identification described herein was substantially different to the pragmatic approach, and followed a more targeted approach by attempting to mimic and exploit elements of the natural, successful immune response to *T. circumcincta* in infected sheep. First, we identified potential vaccine candidate molecules by immunochemical and proteomic analyses; this was done by screening immunoblots of *T. circumcincta* ES material with IgA from infected, immune sheep and comparing these responses to those observed in infected, non-immune sheep or non-infected sheep (Smith et al., 2009). We also identified a homologue of a known protective antigen [Ac-SAA-1 (Zhan et al., 2004)] using bioinformatic analysis of stage-specific cDNA libraries (Nisbet et al., 2008; 2009). Finally, using a combination of these technologies, we identified a suite of potentially immunosuppressive molecules produced by the parasite (McSorley et al., 2010, Nisbet et al., 2010a; 2011). We produced recombinant versions of each of these molecules, examined that they were targets of IgA present in mucus derived from immune sheep and then combined them into a multi-component vaccine which aimed to provoke the host immune system to respond to potentially immunostimulatory molecules (Tci-CF-1, Tci-MEP-1, Tci-ES20, Tci-ASP-1 and Tci-SAA-1) and to produce a possible neutralising effect on putatively immunosuppressive components. The rationale behind using a combination of recombinant molecules, as opposed to single antigens, is as follows: previous vaccination trials using single recombinant antigen preparations of homologues of some of the molecules described herein, in different nematode/host models, have failed. In *O. ostertagi*, for example, the astacin-like metalloproteinase MET-1, which shares >50% amino acid identity with Tci-MEP-1, was selected by immunoscreening but failed to give any protection when used as a single recombinant antigen in a vaccine trial (De Maere et al., 2005). Similarly, recombinant Oo-ASP1, which shares >75% sequence identity with Tci-ASP-1 (Nisbet et al., 2010b), has failed to induce protective immunity in vaccinated calves (Geldhof et al., 2008) and a recombinant version of the *Necator americanus* orthologue of Tci-SAA-1 (Na-SAA-1, 71% amino acid identity) failed to induce significant protection against L3 challenge in a hamster model (Xiao et al., 2008).

The mechanism of action of the vaccine used herein is not yet clear. These nematodes are acquired by ingestion of L3 from pasture. Thereafter, the developing parasites (L3 and L4) and adult worms reside in the host's abomasum. Protective immunity against *T. circumcincta* in sheep exposed to continuous field or experimental trickle challenge has been associated with decreased larval establishment (L3) and development (L3 and L4) in the mucosa and reduced egg output from female worms in the lumen (Balic et al., 2003; Seaton et al., 1989: Smith et al., 1985, 1986; Stear et al., 2004). In the current study, in Trial 2, adult worm burdens in vaccinated and adjuvant only groups were similar at day 84, so it seems unlikely that exclusion and expulsion of incoming L3 or death/delayed development of L4 worms was responsible for the observed reduction in adult parasite numbers at day 112 of that trial. The reduction in the numbers of adult worms may therefore be ascribed to either a direct effect anti-parasitic effect of the induced immune response against the adult worms or a cumulative fitness-reducing effect throughout the life of the worm, culminating in the lower level, or shorter duration, of adult survival.

The immune mechanisms responsible for the observed effects on the parasites are likely to be complex: In naturally-acquired immunity to *T. circumcincta* in sheep roles for immediate hypersensitivity reactions and for larval antigen-specific IgA in gastric secretions have been indicated (Smith et al., 1986; 1987; Stear et al., 1995; 1999; Halliday et al., 2007; Smith et al. 2009). Cellular effectors of the immune response, e.g. γδTCR$^+$ T cells, CD4$^+$ T cells, eosinophils, globular leukocytes and mast cells may also play a role in immunity against *T. circumcincta* in naturally- or experimentally-exposed sheep (e.g. Stear et al., 2002; 2009, Balic et al., 2003; Halliday et al., 2010, Williams 2012).

In conclusion, we have developed a multi-component vaccine against *T. circumcincta* which, in experimental circumstances, reduced mean FECs and mean luminal parasite burdens by >70%. It should be noted that, according to Barnes et al., (1995) it is not essential for a vaccine against parasitic nematodes to be 100% effective in sheep, and "substantial benefits" can be gained by using a vaccine that is 60% effective in 80% of the flock, if the vaccine is based on the stimulation of "natural immunity". On this basis, the results of this study would clearly indicate that the vaccine used here holds much potential. It is not yet clear whether all of the eight recombinant protein components of the vaccine are required for this level of efficacy and further work will seek to clarify this and also to confirm the anti-parasite effects of the 8-protein cocktail vaccine.

REFERENCES

Balic, A., Bowles, V. M., Liu, Y. S. & Meeusen, E. N. Local immune responses in sensitized sheep following challenge infection with *Teladorsagia circumcincta*. *Parasite Immunol*. 25, 371-381 (2003).

Barnes, E. H., Dobson, R. J. & Barger, I. A. Worm control and anthelmintic resistance: adventures with a model. *Parasitology Today* 11, 56-63 (1995).

Bartley, D. J., Jackson, F., Jackson, E. & Sargison, N. Characterisation of two triple resistant field isolates of *Teladorsagia* from Scottish lowland sheep farms. *Vet. Parasitol*. 123, 189-199 (2004).

Cachat, E., Newlands, G. F., Ekoja, S. E., McAllister, H., Smith, W. D. Attempts to immunize sheep against *Haemonchus contortus* using a cocktail of recombinant proteases derived from the protective antigen, H-gal-GP. *Parasite Immunol* 32, 414-419. (2010).

Christie, M. & Jackson, F. Specific identification of strongyle eggs in small samples of sheep faeces. *Res Vet Sci* 32, 113-117 (1982).

De Maere, V., Vercauteren, I., Geldhof, P., Gevaert, K., Vercruysse, J. & Claerebout, E. Molecular analysis of astacin-like metalloproteases of *Ostertagia ostertagi*. *Parasitology* 130, 89-98 (2005).

Geldhof, P., Claerebout, E., Knox, D., Vercauteren, I., Looszova, A. & Vercruysse, J. Vaccination of calves against *Ostertagia ostertagi* with cysteine proteinase enriched protein fractions. *Parasite Immunol*. 24, 263-270 (2002).

Geldhof, P., Vercauteren, I., Vercruysse, J., Knox, D. P., Van Den Broeck, W. & Claerebout, E. Validation of the protective *Ostertagia ostertagi* ES-thiol antigens with different adjuvantia. *Parasite Immunol*. 26, 37-43 (2004).

Geldhof, P., De Maere, V., Vercruysse, J. & Claerebout, E. Recombinant expression systems: the obstacle to helminth vaccines? *Trends Parasitol* 23, 527-532 (2007).

Geldhof, P., Meyvis, Y., Vercruysse, J. & Claerebout E. Vaccine testing of a recombinant activation-associated secreted protein (ASP1) from *Ostertagia ostertagi*. *Parasite Immunol*. 30, 57-60 (2008).

Gibson T. E. & Everett, G. Effect of different levels of intake of *Ostertagia circumcincta* larvae on the faecal egg counts and weight gain of lambs. *J Comp Pathol*. 86, 269-274 (1976).

Halliday, A. M., Routledge, C. M., Smith, S. K., Matthews, J. B. & Smith, W. D. Parasite loss and inhibited development of *Teladorsagia circumcincta* in relation to the kinetics of the local IgA response in sheep. *Parasite Immunol*. 29, 425-434 (2007).

Halliday, A. M., McAllister, H. C. & Smith, W. D. Kinetics of the local immune response in the gastric lymph of lambs after primary and challenge infection with *Teladorsagia circumcincta*. *Parasite Immunol* 32, 81-90 (2010).

Houdijk, J. G., Kyriazakis, I., Jackson, F., Huntley, J. F. & Coop, R. L. Effects of protein supply and reproductive status on local and systemic immune responses to *Teladorsagia circumcincta* in sheep. *Vet Parasitol* 129 105-117 (2005).

Huntley, J. F., Redmond, J., Welfare, W., Brennan, G., Jackson, F., Kooyman, F. & Vervelde, L. Studies on the immunoglobulin E responses to *Teladorsagia circumcincta* in sheep: purification of a major high molecular weight allergen. *Parasite Immunol* 23, 227-235 (2001).

Lawton, D. E., Reynolds, G. W., Hodgkinson, S. M., Pomroy, W. E. & Simpson, H. V. Infection of sheep with adult and larval *Ostertagia circumcincta*: effects on abomasal pH and serum gastrin and pepsinogen. *Int J Parasitol* 26, 1063-1074 (1996).

McSorley, H. J., Grainger, J. R., Harcus, Y. M., Murray, J., Nisbet, A. J., Knox, D. P. & Maizels, R. M. Expression of highly conserved TGF-β family members in the Trichostrongyloid nematodes *Haemonchus contortus, Heligmosomoides polygyrus, Nippostrongylus brasiliensis* and *Teladorsagia circumcincta*. *Parasitology* 137, 159-171 (2010).

Meyvis, Y., Geldhof, P., Gevaert, K., Timmerman, E., Vercruysse, J. & Claerebout, E. Vaccination against *Ostertagia ostertagi* with subfractions of the protective ES-thiol fraction. *Vet. Parasitol*. 149, 239-45 (2007).

Nieuwhof, G. J. & Bishop, S. C. Costs of the major endemic diseases of sheep in Great Britain and the potential benefits of reduction in disease impact. *Animal Sci*. 81, 23-29 (2005).

Nisbet, A. J., MacKellar, A., McLean, K., Brennan, G. P. & Huntley, J. F. Eukaryotic expression of recombinant Pso o 1, an allergen from *Psoroptes ovis*, and its localization in the mite. *Parasitology* 134, 83-89 (2007).

Nisbet, A. J., Redmond, D. L., Matthews, J. B., Watkins, C., Yaga, R., Jones, J. T., & Knox, D. P. Stage-specific gene expression in *Teladorsagia circumcincta* (Nematoda: Strongylida) infective larvae and early parasitic stages. *Int J Parasitol* 38, 829-338 (2008).

Nisbet, A. J., Knox, D. P., McNair, C. M., Meikle, L. I., Smith, S. K., Wildblood, L. A. & Matthews, J. B. Immune recognition of the surface associated antigen, Tc-SAA-1, from infective larvae of *Teladorsagia circumcincta*. *Parasite Immunol*. 31, 32-40 (2009).

Nisbet, A. J., Bell, N. E. V., McNeilly, T. N., Knox, D. P., Maizels, R. M., Meikle, L. I., Wildblood, L. A. & Matthews, J. B. A macrophage migration inhibitory factor-like tautomerase from *Teladorsagia circumcincta* (Nematoda: Strongylida). *Parasite Immunol*. 32, 503-511 (2010a).

Nisbet, A. J., Smith, S. K., Armstrong, S., Meikle, L. I., Wildblood, L. A., Beynon, R. J. & Matthews, J. B. *Teladorsagia circumcincta*: Activation-associated secreted proteins in excretory/secretory products of fourth stage larvae are targets of early IgA responses in infected sheep. *Exp Parasitol* 125, 329-337 (2010b).

Nisbet, A. J., Zarlenga, D. S., Knox, D. P., Meikle, L. I., Wildblood L. A. & Matthews, J. B. A calcium-activated apyrase from *Teladorsagia circumcincta*: an excretory/secretory antigen capable of modulating host immune responses? *Parasite Immunol* in press (2011).

Redmond, D. L., Smith, S. K., Halliday, A., Smith, W. D., Jackson, F., Knox, D. P. & Matthews, J. B. An immunogenic cathepsin F secreted by the parasitic stages of *Teladorsagia circumcincta*. *Int J Parasitol* 36, 277-286 (2006).

Seaton, D. S., Jackson, F., Smith, W. D. & Angus, K. W. Development of immunity to incoming radiolabelled larvae in lambs continuously infected with *Ostertagla circumcincta*. *Res. Vet. Sci.* 46, 241-246 (1989).

Singleton, D. R., Stear, M. J. & Matthews, L. A mechanistic model of developing immunity to *Teladorsagia circumcincta* infection in lambs. *Parasitology DOI:* 10.1017/S0031182010001289 (2011).

Smith, S. K. Nisbet, A. J., Meikle, L., Inglis, N., Sales, J., Beynon, R. J. & Matthews, J. B. Proteomic analysis of excretory/secretory products released by *Teladorsagia circumcincta* larvae early post-infection *Parasite Immunol* 31, 10-19 (2009).

Smith, W. D., Jackson, F., Jackson, E. & Williams, J. Age immunity to *Ostertagia circumcincta*: comparison of the local immune responses of 4½- and 10-month-old lambs. *J. Comp. Pathol.* 95, 235-245 (1985).

Smith, W. D., Jackson, F., Jackson, E., Graham, R., Williams, J., Willadsen, S. M & Fehilly, C. B. Transfer of immunity to *Ostertagia circumcincta* and IgA memory between identical sheep by lymphocytes collected from gastric lymph. *Res. Vet. Sci.* 41, 300-306 (1986).

Smith, W. D., Jackson, F., Graham, R., Jackson, E. & Williams, J. Mucosal IgA production and lymph cell traffic following prolonged low level infections of *Ostertagia circumcincta* in sheep. *Res Vet Sci* 43, 320-326 (1987).

Smith, W. D., Pettit, D. & Smith, S. K. Cross-protection studies with gut membrane glycoproteins from *Haemonchus contortus* and *Teladorsagia circumcincta*. *Parasite Immunol.* 23, 203-211 (2001).

Stear, M. J., Bairden, K., Innocent, G. T., Mitchell, S., Strain, S. & Bishop, S. C. The relationship between IgA activity against 4th-stage larvae and density-dependent effects on the number of 4th-stage larvae of *Teladorsagia circumcincta* in naturally infected sheep. *Parasitology* 129, 363-369 (2004).

Taylor S M, Kenny J, Edgar H W, Ellison S, Ferguson L (1997) Efficacy of moxidectin, ivermectin and albendazole oral drenches for suppression of periparturient rise in ewe worm egg output and reduction of anthelmintic treatment for lambs. Vet Record 141: 357-360.

Wedrychowicz, H., Bairden, K., Tait, A. & Holmes, P. H. Immune responses of sheep to surface antigens of infective larvae of *Ostertagia circumcincta*. *Parasite Immunol*, 14: 249-266 (1992).

Wedrychowicz, H., Bairden, K., Dunlop, E. M., Holmes, P. H. & Tait, A. Immune response of lambs to vaccination with *Ostertagia circumcincta* surface antigens eliciting bile antibody responses. *Int J Parasitol* 25, 1111-1121 (1995).

Wrigley, J., McArthur, M., McKenna, P. B. & Mariadass, B. Resistance to a triple combination of broad-spectrum anthelmintics in naturally-acquired *Ostertagia circumcincta* infections in sheep. N. Z. Vet. J. 54, 47-49 (2006).

Xiao, S., Zhan, B., Xue, J., Goud, G. N., Loukas, A., Liu, Y., Williamson, A., Liu, S., Deumic, V. & Hotez, P. The evaluation of recombinant hookworm antigens as vaccines in hamsters (*Mesocricetus auratus*) challenged with human hookworm, *Necator americanus*. *Exp Parasitol* 118, 32-40 (2008).

Zhan, B., Wang, Y., Liu, Y., Williamson, A. Loukas, A., Hawdon, J. M., Xue, H. C., Xiao, S. H. & Hotez, P. J. Ac-SAA-1, an immunodominant 16 kDa surface-associated antigen of infective larvae and adults of *Ancylostoma caninum*. *Int J Parasitol* 34, 1037-1045 (2004).

---

The invention claimed is:

1. A method of raising an immune response to *Teladorsagia* in an animal, said method comprising a step of administering to an animal, an immunogenic amount of *Teladorsagia* astacin-like metalloproteinase-1 (MEP-1) antigen, wherein the MEP-1 antigen comprises a sequence that has at least 95% identity to the amino acid sequence of SEQ ID NO:7.

2. The method of claim 1, wherein the animal is an ovine animal, a bovine animal, a sheep or a goat.

3. The method of claim 1, wherein the antigen(s) is/are recombinant antigens.

4. The method of claim 1, wherein the immune response is a protective immune response.

5. The method of claim 1, wherein the immune response reduces host *T. circumcincta* faecal egg counts (FECs) and luminal *T. circumcincta* burdens.

6. The method of claim 1, wherein the antigen(s) are admixed with another vaccine, polypeptide, adjuvant, diluent or excipient.

7. The method of claim 1, wherein the method further comprises a step of administering to an animal, an immunogenic amount of one or more *T. circumcincta* (Tci) antigens selected from the group consisting of:

(i) cathepsin F-1 (Tci-CF-1);
(ii) calcium-dependent apyrase-1 (Tci-APY-1);
(iii) excretory/secretory protein (unknown function: Tci-ES20);
(iv) transforming growth protein 2-like protein (a TGFβ homologue: Tci-TGH-2);
(v) activation associated secretory protein (Tci-ASP-1);
(vi) macrophage migration inhibitory factor (Tci-MIF-1);
(vii) surface associated antigen (Tci-SAA-1); and
(viii) an antigen encoded by a sequence exhibiting at least 95% identity with the amino acid sequence of SEQ ID NO: 1, 2, 3, 4, 5, 6 or 8.

8. The method of claim 1, wherein the method further comprises a step of administering to an animal an immunogenic amount of *T. circumcincta* (Tci) antigen calcium-dependent apyrase-1 (Tci-APY-1).

* * * * *